United States Patent
Jacobson et al.

(10) Patent No.: US 8,421,457 B2
(45) Date of Patent: Apr. 16, 2013

(54) METHODS AND SYSTEMS FOR MAGNETICALLY RESONATING BOTH A SUBJECT AND A SUBSTANCE ADMINISTERED TO THE SUBJECT

(75) Inventors: Jerry I Jacobson, Jupiter, FL (US); Allen Braswell, Jr., Littleton, CO (US); Christopher M Rose, Essex Jct., VT (US); William Pottow, Charlotte, VT (US); John Cronin, Jericho, VT (US)

(73) Assignee: Applied Magnetics, LLC, Littleton, CO (US)

( * ) Notice: Subject to any disclaimer, the term of this patent is extended or adjusted under 35 U.S.C. 154(b) by 478 days.

(21) Appl. No.: 12/548,802

(22) Filed: Aug. 27, 2009

(65) Prior Publication Data

US 2010/0072996 A1    Mar. 25, 2010

Related U.S. Application Data

(60) Provisional application No. 61/092,169, filed on Aug. 27, 2008.

(51) Int. Cl.
*G01R 33/281* (2006.01)
*G01V 3/00* (2006.01)
*A61B 5/05* (2006.01)

(52) U.S. Cl.
USPC ........... 324/309; 324/307; 324/318; 600/420; 600/431

(58) Field of Classification Search .......... 324/300–322; 600/407–435, 13–14; 382/128–131; 607/9; 706/45

See application file for complete search history.

(56) References Cited

U.S. PATENT DOCUMENTS

| | | | |
|---|---|---|---|
| 3,659,282 A | 4/1972 | Tada | |
| 4,723,536 A * | 2/1988 | Rauscher et al. | 600/14 |
| 4,889,526 A * | 12/1989 | Rauscher et al. | 600/14 |
| 5,453,072 A | 9/1995 | Anninos et al. | |
| 6,099,459 A | 8/2000 | Jacobson | |
| 6,155,966 A | 12/2000 | Parker | |
| 6,301,506 B1 | 10/2001 | den Boer et al. | |
| 6,470,220 B1 * | 10/2002 | Kraus et al. | 607/103 |
| 6,527,697 B2 | 3/2003 | Bashford | |
| 6,804,558 B2 | 10/2004 | Haller | |

(Continued)

FOREIGN PATENT DOCUMENTS

| | | |
|---|---|---|
| DE | 10157024 A1 | 5/2003 |
| WO | 2007051419 A1 | 5/2007 |

OTHER PUBLICATIONS

Jacobson, J. I., "Jacobson Resonance: The Quantum-mechanical Basis for a Novel Radiological Approach to Treating Cancer and Aids," Frontier Perspectives, vol. 6, No. 1, Fall/Winter 19 96, pp. 17-26.*

(Continued)

*Primary Examiner* — Melissa Koval
*Assistant Examiner* — Tiffany Fetzner
(74) *Attorney, Agent, or Firm* — Kilpatrick Townsend & Stockton LLP

(57) ABSTRACT

Embodiments of the current invention include a magnetic resonance system including a magnetic resonance device and a substance to be introduced to a subject in accordance with a treatment. Further embodiments of the current invention include a method of using a magnetic resonance system including administering a substance to a subject and providing magnetic resonance to the subject.

26 Claims, 4 Drawing Sheets

U.S. PATENT DOCUMENTS

| | | | |
|---|---|---|---|
| 6,842,645 B2 | 1/2005 | Dalal | |
| 6,858,000 B1 | 2/2005 | Schukin et al. | |
| 6,995,700 B2 | 2/2006 | Roger et al. | |
| 7,186,209 B2* | 3/2007 | Jacobson et al. | 600/13 |
| 7,324,850 B2 | 1/2008 | Persen | |
| 7,395,117 B2 | 7/2008 | Mazar | |
| 2004/0136489 A1 | 7/2004 | Takahashi et al. | |
| 2004/0181115 A1 | 9/2004 | Sandyk et al. | |
| 2004/0254419 A1* | 12/2004 | Wang et al. | 600/8 |
| 2005/0025797 A1* | 2/2005 | Wang et al. | 424/422 |
| 2005/0079132 A1* | 4/2005 | Wang et al. | 424/1.11 |
| 2005/0080459 A1* | 4/2005 | Jacobson et al. | 607/9 |
| 2005/0107870 A1* | 5/2005 | Wang et al. | 623/1.44 |
| 2005/0283330 A1 | 12/2005 | Laraia et al. | |
| 2007/0004957 A1 | 1/2007 | Hilburg | |
| 2007/0010702 A1* | 1/2007 | Wang et al. | 600/8 |
| 2008/0039904 A1* | 2/2008 | Bulkes et al. | 607/62 |
| 2008/0213382 A1* | 9/2008 | Ivkov et al. | 424/497 |
| 2008/0221429 A1* | 9/2008 | Nezafat et al. | 600/410 |
| 2008/0317317 A1* | 12/2008 | Shekhar et al. | 382/131 |
| 2010/0057655 A1* | 3/2010 | Jacobson et al. | 706/45 |
| 2010/0072996 A1* | 3/2010 | Jacobson et al. | 324/309 |
| 2011/0044524 A1* | 2/2011 | Wang et al. | 382/131 |
| 2012/0157824 A1* | 6/2012 | Bossmann et al. | 600/420 |

OTHER PUBLICATIONS

Jacobson, J. I., "A Possible, Physical Mechanism in the Treatment of Neurologic Disorders with Externally Applied Pico Tesla Magnetic Fields," Physiol. Chem. Phys. & Med. NMR, vol. 26, 1994, pp. 287-297.*

Sandyk, R., "Clinical Case Report Magnetic Fields in the Treatment of Parkinson's Disease," Intern. J. Neuroscience, vol. 63, 1992, pp. 141-150.*

Sandyk, R., "Clinical Case Report Successful Treatment of Multiple Sclerosis With Magnetic Fields," Intern. J. Neuroscience, vol. 66, 1992, pp. 237-250.*

Sandyk, R., "Alzheimer's Disease: Improvement of Visual Memory and Visuoconstructive Performance by Treatment with Picotesla Range Magnetic Fields," Intern. J. Neuroscience, vol. 76, 1994, pp. 185-225.*

International Preliminary Report on Patentability mailed Mar. 10, 2011 for corresponding International Application No. PCT/US2009/054803.

International Preliminary Report on Patentability mailed Mar. 10, 2011 for corresponding International Application No. PCT/US2009/055183.

International Preliminary Report on Patentability mailed Jan. 20, 2011 for corresponding International Application No. PCT/US2009/050114.

International Search Report and Written Opinion mailed Nov. 5, 2009 corresponding to PCT Patent Application No. PCT/US2009/054803.

International Search Report and Written Opinion mailed Nov. 6, 2009 corresponding to PCT Patent Application No. PCT/US2009/050114.

* cited by examiner

METHODS AND SYSTEMS FOR MAGNETICALLY RESONATING BOTH A SUBJECT AND A SUBSTANCE ADMINISTERED TO THE SUBJECT

CROSS-REFERENCE TO RELATED APPLICATION

This application claims the benefit of provisional U.S. Provisional Patent Application Ser. No. 61/092,169, for "Systems and Methods for Magnetically Resonating Both a Subject and Substance Introduced Into the Body of the Subject," filed Aug. 27, 2008, the entirety of which is herein incorporated by reference.

FIELD OF THE INVENTION

The present invention relates to the field of magnetic resonance. In particular, the present invention is directed to a magnetic resonance system for and method of magnetically resonating both a substance and the tissues, cells, molecules, and/or atoms of a subject before, concomitant with, or after introducing the substance to the body of the subject.

BACKGROUND

Magnetic resonance is a widely practiced and growing alternative treatment for many indications (i.e., illness, disease, medical condition, or ailment). Magnetic resonance devices are a natural and economical means of treating body pains and common injuries. Many methods have been used to apply magnets to comfort or heal body areas and, thereby, avoiding the use of injections, pills, salves, or body-invasive procedures. Overall, the basis of magnetic resonance involves artificially produced fields. These fields may interact with components such as but not limited to, atomic or molecular components of living tissue which then have a beneficial effect on that living tissue.

One form of magnetic resonance uses static magnetic fields. Static magnetic fields are produced by permanent magnets that may be incorporated into common items, such as bracelets, belts, back pads, mattress pads, and mattresses. It is believed that static magnetic fields have some efficacy in the treatment of broken bones and soft tissue injuries, and tend to promote the circulation of blood as well as relieve stiffness in muscles. More recent attempts to employ the therapeutic effects of magnetic fields have focused on devices that generate an electromagnetic field, and methods of treatment that employ such devices in conjunction with computers.

Using beneficial substances to treat indications is also known in the art. Such substances may be used for a variety of purposes, including to treat symptoms of a disease, illness, injury, or other indication; as well as for general health and wellness or any other purpose. There is a need for a method and system for providing magnetic resonance to a subject before, concomitant with, or after administering a substance to the subject.

SUMMARY

One embodiment of the present invention comprises a magnetic resonance system comprising a magnetic resonance (MR) device. Further, an embodiment may comprise a substance to be introduced to a subject's body in accordance with a treatment.

Another embodiment of the present invention comprises a method of using a magnetic resonance system comprising administering a substance to a subject and providing a magnetic field to the subject either before, concomitant with, or after administration of the substance. Additionally, the method may comprise the initial step of generating a treatment regimen based on analyzing data.

Yet another embodiment of the present invention comprises a method of treating a human, animal, or plant subject with an indication, the method comprising administering a substance and magnetic resonance, wherein the magnetic resonance is given before, after, or concomitant with the beneficial substance.

Another embodiment of the present invention comprises a method of treating a subject that reduces the amount of a substance required to achieve a result, or that increases the efficacy of an amount of a substance by exposing the subject to a magnetic field before, concomitant with, or after the administration of the substance.

These embodiments are mentioned not to limit or define the invention, but to provide examples of embodiments of embodiments of the invention to aid in understanding thereof. Embodiments are discussed in the Detailed Description, and further description of the invention is provided there. Advantages offered by the various embodiments of the present invention may be further understood by examining this specification.

BRIEF DESCRIPTION OF THE DRAWINGS

These and other features, aspects, and advantages of the present invention are better understood when the following Detailed Description is read with reference to the accompanying drawings, wherein.

DETAILED DESCRIPTION

Figure 1:
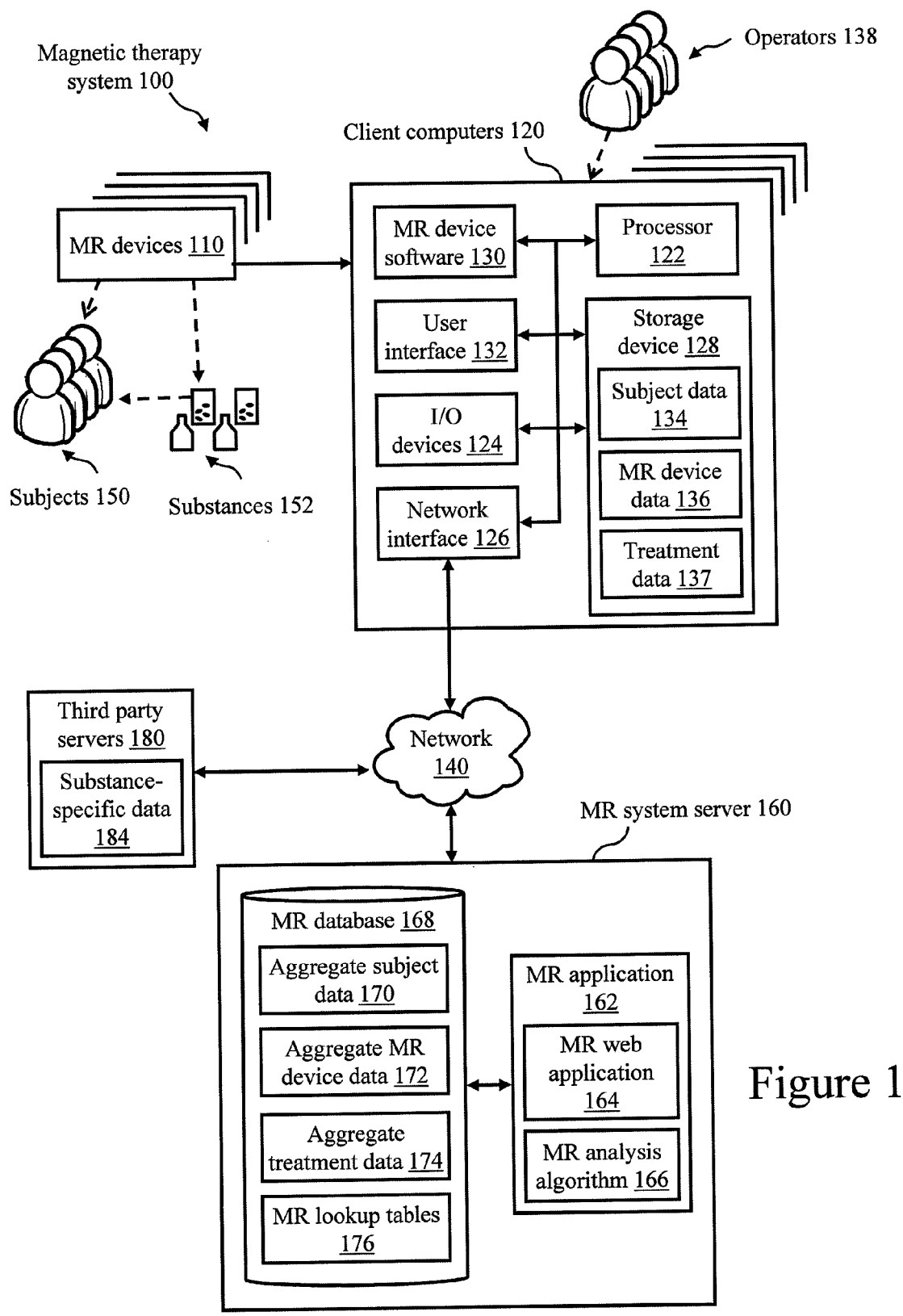
FIG. 1 illustrates a functional block diagram of a magnetic resonance system according to one embodiment of the invention.

There is need in the art for alternative approaches to magnetic resonance as a treatment for various indications. An indication may be an illness, disease, medical condition, injury, or any other ailment. Embodiments of the present invention provide magnetic resonance systems for, and methods of, magnetically resonating both a substance and the tissues, cells, molecules, and/or atoms of a subject before, concomitant with, or after administering the substance to the subject. Embodiments of the magnetic resonance system of the invention may also provide a network of magnetic resonance devices and methods by which both the subject and the substance are exposed to magnetic energy before, concomitant with, or after the substance has been administered to (e.g., ingested, injected, applied topically, or transdermally) the body of the subject of the magnetic resonance treatment. In doing so, the efficacy of the substance for affecting a certain indication may be improved.

Additionally, embodiments of the magnetic resonance system of the invention can provide a mechanism by which a recommended magnetic resonance treatment regimen may be generated for a certain subject that has a certain indication (i.e., illness, disease, medical condition, or ailment). The recommended magnetic resonance treatment regimen may be based on the analysis of a collection of empirical and/or scientific data that may include specific treatment information of substantially similar subjects that have substantially similar indications.

For example, one embodiment of the present invention provides a magnetic resonance system comprising a magnetic therapy device and a substance to be administered to a subject in accordance with a treatment, wherein the subject is treated with magnetic resonance before, concomitant with, or after introduction of the substance. In one embodiment, the substance is a beneficial substance in that it may improve the health or wellness of the subject.

In one embodiment, the system may comprise a computer comprising a processor. The system may further comprise magnetic resonance device software residing in the memory of the computer and executable by the processor of the computer. Further, the computer may comprise a storage device capable of storing data in electronic format. The storage device may contain one or more of: subject data, magnetic resonance device data, and treatment data.

In a further embodiment, the computer is capable of receiving data from an external source. The data from an outside source may comprise information regarding the substance. In one embodiment, the data comprises information regarding the subject. In a further embodiment, the data comprises information regarding the treatment. Additionally or alternatively, the data may comprise the order in which one or more magnetic signals are provided.

In one embodiment, the system comprises a server capable of communicating with the computer. The server may include a database. In one embodiment, the server further comprises a magnetic resonance application residing in the memory of the server and executable by the processor of the server. The magnetic resonance application may comprise a magnetic resonance web application. Additionally or alternatively, the magnetic resonance application may comprise a magnetic resonance analysis algorithm.

In one embodiment, the database comprises a magnetic resonance (MR) treatment database. The database may contain at least one of: aggregate subject data, aggregate magnetic resonance device data, aggregate treatment data, aggregate substance data, and a magnetic resonance treatment lookup table. Aggregate subject data may include a collection of data from a plurality of subjects. Such data may include height, weight, age, sex, medical history, and/or any other information about a subject. Aggregate MR device data may include a collection of data about a plurality of MR devices and/or data about a plurality of settings used on one or more MR devices. Such data may include information about coil(s), location (e.g., latitude and/or longitude), settings, and/or any other data about a magnetic treatment device. Aggregate MR treatment data may include a collection of data regarding a plurality of treatments provided. Such data may include flux density, waveform, amplitude, frequency, duration of an individual signal step, the subject's response, and/or any other information about a substance or an MR treatment. Aggregate substance data may include a collection of data about a plurality of substances that may be administered in the course of one or more treatments. Such data may include type of substance, name of substance, amount of substance, the indication for which the substance is used, interaction between one substance and other substance(s), and/or any other information about a substance. A magnetic resonance lookup table may include a collection of data regarding one or more magnetic treatments. Or, in some cases, data specific to a single subject, device, or MR treatment may be used.

In one embodiment, generating an MR treatment regimen based on analyzing data comprises the steps of analyzing MR data for prior treatment records of the subject, providing data regarding the subject's prior response to the MR treatment, and/or determining if a treatment is the best match to the subject. The step of generating a treatment regimen based on analyzing data may comprise the steps of analyzing data for positive prior treatment records of like-situated subjects, and determining the treatment that is the best match to the subject. A treatment regimen may include information regarding the magnetic resonance to be provided in a given situation. This may include one or more of: waveform, flux density, frequency, duration, number of treatments, and intervals between treatments. A like-situated subject may be a subject with substantially matching user information and/or indications.

In one embodiment, the step of generating a treatment regimen based on analyzing data comprises the steps of analyzing subject population trends, and determining the treatment that is the best match to the subject. A subject population trend may include data regarding changes in information about a plurality of subjects. For example, a subject population trend may include a rate of change in one or more symptoms over a period of time for a plurality of subjects when exposed to a particular MR treatment or treatments.

In some embodiments, the substance is administered to the subject after the magnetic resonance has begun. In further embodiments, the substance is administered to the subject before the magnetic resonance begins. Additionally or in the alternative, the substance may be administered concomitant with (i.e., during) the MR treatment.

In some embodiments, the present invention further comprises storing data concerning the treatment regimen.

In other embodiments, the present invention comprises a method of using a magnetic resonance system comprising administering a substance to a subject and providing a magnetic field to the subject before, concomitant with, or after administration of the substance.

In certain embodiments, the method may comprise an initial step of generating a treatment regimen based on analyzing data. In some embodiments, the data comprises at least one of MR data, MR subject data, MR device data, or MR lookup tables such as those described herein. In various embodiments, the data may comprise data specific to an individual subject, substance, treatment, or device.

In another embodiment, generating a treatment regimen based on analyzing data comprises the steps of analyzing data for at least one positive prior treatment record of the subject and determining the treatment that is the best match to the subject.

In one embodiment, generating a treatment regimen based on analyzing data comprises the steps of analyzing data for positive prior treatment records of like-situated subjects, and determining the treatment that is the best match to the subject.

In further embodiments, generating a treatment regimen based on analyzing data comprises the steps of analyzing subject population trends, and determining the treatment that is the best match to the subject.

Depending on the condition, indication, or for any other reason, the substance may be introduced at various times vis-à-vis the MR treatment. In an embodiment, the substance is introduced after the magnetic field has begun to be provided.

In an additional or alternative embodiment, the substance is introduced before the magnetic field has begun to be provided.

In an additional or alternative embodiment, the substance is introduced concomitant with providing the magnetic field.

In certain embodiments, the subject is monitored before, after, and/or during the treatment. For example, in some embodiments, making the decision to continue or end treatment may be based at least in part on the monitoring of the subject. In another embodiment, adjusting (modifying) the treatment regimen (or a future treatment) is based at least in part on the monitoring of the subject.

In certain embodiments, the method may comprise the step of storing data concerning the treatment regimen. Methods for storing the data may employ a computer, web server, and/or other components as described herein or known in the art.

In other embodiments, the present invention comprises a method of treating a human, animal, or plant subject with an indication. The method, in certain embodiments, may comprise administering a substance and magnetic resonance, wherein the magnetic resonance is given before, after, or concomitant with the substance. In one embodiment, the substance is a beneficial substance, in that the substance has a beneficial or wellness-promoting effect on the subject.

In some embodiments, the substance is a beneficial substance, such that the substance has the capacity to ameliorate at least in part a symptom associated with the indication.

In one embodiment, the indication comprises at least one of Parkinson's disease, diabetes, cancer, osteoarthritis, migraine, headache, fibromyalgia, chronic fatigue syndrome, pain, sports injury, accident injury, stiffness, back pain, diabetic neuropathy, high cholesterol, enlarged prostate, cardiac arrhythmia, tachycardia, atrial fibrillation, ventricular fibrillation, AIDS, Alzheimer's disease, multiple sclerosis, amyotrophic lateral sclerosis, muscular dystrophy, attention deficit disorder, attention deficit hyperactive disorder, cerebral palsy, depression, or schizophrenia.

In one embodiment, the substance comprises at least one of a drug for Parkinson's disease (e.g., Levodopa), a beta blocker, a cancer drug, a diabetes drug, aspirin, ibuprofen, a migraine drug, a pain reliever, Naproxen, a cholesterol drug, or a drug to improve function of a specific organ (e.g., prostate, thyroid, liver, or heart).

In one embodiment, administering magnetic resonance comprises providing a magnetic field with a flux density range of about 1 gauss to about $10^{-50}$ gauss. In other embodiments, administering magnetic resonance comprises providing a magnetic field with a flux density range of about $10^{-5}$ gauss to about $10^{-12}$ gauss, about 0.01 micro-gauss to about 0.6 micro-gauss as described herein, or ranges within these ranges may be used.

For example, in one embodiment, the indication comprises Parkinson's disease. Where the indication is Parkinson's disease, embodiments of the method may comprise administering magnetic resonance to provide a magnetic field with a flux density range of about $6.6 \times 10^{-8}$ gauss to about $7.8 \times 10^{-8}$ gauss. Or the method may comprise administering magnetic resonance to provide a magnetic field with a frequency range of about 1.0 Hz to about 150 Hz, about 1.8 Hz to about 140 Hz, about 1.8 Hz to about 7.8 Hz, or ranges within these ranges may be used.

In one embodiment, the indication comprises diabetes. Where the indication is diabetes, the method may comprise administering magnetic resonance to provide a magnetic field with a flux density range of about $5 \times 10^{-7}$ gauss to about $1 \times 10^{-8}$ gauss or about 2.156 Hz to about 13.992 Hz.

In one embodiment, the indication comprises diabetic neuropathy. Where the indication is diabetic neuropathy, the method may comprise administering magnetic resonance to provide a magnetic field with a flux density range of about $4.992 \times 10^{-7}$ gauss to about $5.2 \times 10^{-7}$ gauss and a frequency range from about 13.992 Hz to about 14.2 Hz, or ranges within this range may be used.

Other embodiments of the present invention may provide methods of treating a subject that reduce the amount of a substance required to achieve a beneficial result or that increases the efficacy of an amount of a substance by exposing the subject to a magnetic field before, concomitant with, or after the administration of the beneficial substance.

Thus, embodiments of the present invention provide methods and systems for magnetically resonating both a subject and a substance administered to the body of the subject. Numerous modifications and adaptations are apparent to those skilled in the art without departing from the scope of this disclosure.

Embodiments of the magnetic resonance system described herein provide a network of MR devices by which both a subject and a substance are exposed to magnetic energy before, concomitant with, or after the substance has been administered to (e.g., ingested, injected, applied topically or transdermally) the body of the subject. In doing so, the efficacy of the substance for affecting a certain indication may be improved. In one embodiment, by consuming a certain substance of interest just prior to or while the subject is in the process of receiving a magnetic resonance treatment via a certain magnetic resonance devices, the performance of the substance may be improved and, thus, the efficacy of the substance may be improved. Specifically, such techniques may enhance the integration and utilization of the substance. For example, one or more of the following improvements may result from such techniques: improved absorption, improved interaction with body parts, improved metabolic processes, and improved rate of penetration or interaction in target tissues, cells, molecules, atoms, and/or subatomic species of the subject, while the substances are being absorbed into the body of the subject. Additionally, a magnetic treatment analysis algorithm and/or magnetic treatment application of a magnetic resonance system server of the magnetic resonance system of the invention may be used to provide a mechanism by which a recommended magnetic resonance treatment regimen may be generated for a certain subject that has a certain indication (i.e., illness, disease, medical condition, or ailment) and is ingesting certain substances (i.e., drugs, pharmaceuticals, injectibles, and the like) as prescribed by their physician. The recommended magnetic resonance treatment regimen may be based on the analysis of a collection of empirical and/or scientific data within a magnetic treatment database that may include specific treatment information of substantially similar subjects that have substantially similar indications and are ingesting substantially similar substances.

One example benefit of improving the efficacy of certain substances by use of the magnetic resonance (MR) system of the invention is that the dosage of the substance may be reduced, which may result in reduced side effects and reduced cost.

While the MR system of the invention may be described in the context of treating humans before, concomitant with, or after consuming a substance, the MR system of the invention is not limited to humans only. In alternative embodiments, other living systems, such as animals and plants, may be treated before, concomitant with, or after a substance has been administered to the other living systems.

The term "substance" or "beneficial substance" is used herein to describe any substance that is provided to a subject in order to yield an improved condition for the subject. Beneficial substances include, without limitation, nanoparticles (nanotherapeutics and the like), gene therapy constructs, growth hormones, water, beverages, foods, nutraceuticals, pharmaceuticals, drugs, and the like. A beneficial substance may include a therapeutic substance. The term "subject" is used herein to describe any living system, such as any living animal, plant, and/or human, that may be exposed to magnetic resonance treatment by use of the MR system of the invention. The subject may include any user of the MR system in any location, for example at home. In one embodiment, the subject may be a "patient" used herein to refer to a subject who is receiving medical treatment. Thus, the term "subject" is used herein to include a patient or any other person, animal, plant, or object upon which the MR system operates. The term "practitioner" is used herein to include, for example, physicians, physician assistants (PA), nurses, any other health care provider, or other professionals involved in complementary alternative medicine, such as chiropractors or acupuncturists. In certain embodiments, the practitioner is also the subject. The term "research personnel" used herein includes, for example, clinical groups, medical scientists, or regulatory agencies. Additionally, the term "service personnel" includes, for example, device manufacturers, MR system maintenance personnel, database specialists, or computer specialists. All references to MR systems include electro-gravitational systems. The term "concomitant" used herein means occurring at the same time. For example, when a subject takes a substance concomitant with a treatment, there is at least some period of time that both events are occurring—i.e., the subject is being treated while taking the substance. Even if one event starts or ends before the other, the two events are concomitant as long as there is some temporal overlap.

FIG. 1 illustrates a functional block diagram of a magnetic resonance system according to one embodiment of the invention. In one embodiment, the MR system 100 is an example of a system for magnetically resonating a substance before, concomitant with, or after being administered to the subject of the treatment. The MR system 100 is also an example of a system that is suitable for automatically generating a recommended magnetic resonance treatment regimen.

In some embodiments, the MR system 100 may include one or more MR devices 110. In one embodiment, the MR system 100 includes one or more client computers 120. The one or more MR devices 110 and/or respective client computers 120 may be associated with, for example, one or more facilities (not shown) that provide magnetic resonance treatment. In various embodiments, the one or more facilities include one or more of: doctors' offices, hospitals, clinics, any other health care facilities, research laboratories, retailers, pharmacies, salons, heath clubs, and/or spas. Additionally, one or more MR devices 110 and/or respective client computers 120 may be associated with facilitates related to living plants and/or animals. In some embodiments, the MR system 100 is a device-enabled system, within which the enabling device is, for example, the one or more MR devices 110 that provide treatment of subjects via electromagnetic energy.

In some embodiments, the one or more MR devices 110 may include any device that is capable of applying magnetic energy to a subject. In further embodiments, the one or more MR devices 110 are capable of applying magnetic energy to a subject before, concomitant with, or after the subject has consumed, a substance 152, as for example, water and/or other substances, such as beverages, foods, nutraceuticals, pharmaceuticals, drugs, and the like, in order to beneficially restructure and/or enhance the interaction between the substances and certain tissues, cells, molecules, atoms, and/or subatomic species of the subject, while the substances are being absorbed into the body of the subject. In particular, each MR device 110 may be any device that is capable of generating an electromagnetic field of a specified, but variable, flux density. Further, each MR device 110 may be capable of generating a specified, but variable, frequency.

In some embodiments, the MR device 110 may be capable of producing an electromagnetic field with a variety of flux density ranges, including, for example, one or more of the following: from about 1.0 gauss to about $10^{-50}$ gauss, or ranges within this range such as but not limited to the following: from about $10^{-10}$ gauss to $10^{-50}$ gauss; from about $10^{-20}$ gauss to $10^{-40}$ gauss; from about $10^{-5}$ gauss to $10^{-10}$ gauss; and from about $10^{-3}$ gauss to $10^{-6}$ gauss. In some embodiments, the MR device 110 may be capable of producing a flux density window in a variety of ranges including from about 0.1 to about 0.8 gauss, about 0.2 gauss to about 0.7 gauss, or ranges within this range such as but not limited to the following: from about 0.2 gauss to about 0.6 gauss; from about 0.4 gauss to about 0.7 gauss; from about 0.2 gauss to about 0.4 gauss; from about 0.3 gauss to about 0.5 gauss; and from about 0.2 gauss to about 0.3 gauss. Or ranges from about 0.005 gauss to about $1 \times 10^{-6}$ gauss, about 0.1 gauss to about $0.6 \times 10^{-6}$ gauss, or about $0.01 \times 10^{-6}$ gauss to about $0.53 \times 10^{-6}$ gauss may be used. In some embodiments, the MR device 110 may be capable of producing a frequency in a variety of ranges, including from about 0 Hertz to about 1000 Hertz, or ranges within this range such as but not limited to the following: from about 0 Hertz to about 900 Hertz; from about 0 Hertz to about 800 Hertz; from about 0 Hertz to about 500 Hertz; from about 5 Hertz to about 800 Hertz; from about 0 Hertz to about 300 Hertz; from about 10 Hertz to about 100 Hertz, and from about 0.2799 Hz to about 14.84 Hz. Or, ranges within these ranges may be used.

In various embodiments, the preceding ranges may vary depending on the subject, substance, and/or intended results of the magnetic resonance treatment regimen. Examples of settings within the specified ranges include, but are not limited to: $0.075 \times 10^{-6}$ gauss at 2.1 Hz, $0.032 \times 10^{-6}$ gauss at 0.89 Hz, $0.343 \times 10^{-6}$ gauss at 9.6 Hz, 0.2 gauss at 5 Hz, 0.3 gauss at 1 Hz, and 0.5 gauss at 7 Hz. Selected ranges for various indications are provided herein.

In various embodiments, clinically efficacious pico-Tesla ranges are limitative-dependent upon other variables. These variables may include indication(s), condition(s), syndrome(s), disease(s), illness(es), injury(ies), or any other relevant factor(s). Such variable(s) may warrant usage of other signal parameters (e.g., concomitantly utilized) to accommodate the variable(s). For example, prostate cancer that has metastasized may indicate usage of flux densities that are as low as $10^{-20}$ gauss, or as high as $10^{-5}$ gauss; with frequencies ranging from 0 Hz to 280 Hz, or ranges within these ranges. Another example could be cited for diabetic neuropathy, wherein signal parameters might be indicated as low as $0.02 \times 10^{-6}$ gauss at 0.6 Hz to accommodate conditions requiring further decrease in inflammation, as well as associated rigidity in body parts. Another example could be cited for migraine/headache wherein a tumor or lesion might require extended signal parameters as high as $10^{-5}$ gauss at 280 Hz, or as low as $10^{-18}$ gauss at 0 Hz to 1000 Hz.

In alternative or additional embodiments, MR treatment below the pico-Tesla range may be provided. For example, such ranges may be used when the fundamental targets include sub-atomic particles (e.g., electrons, protons, mesons).

In still other embodiments, targets may include small molecular species (e.g., trace metals, eg. Ca++, K+, Na+, CL−, Mg++) or water molecules. In such cases, signal parameters from $10^{-20}$ gauss to about $10^{-8}$ gauss may be indicated, or ranges within this range, in addition to ranges specified.

Additionally, certain MR devices 110 may be whole body MR devices, meaning MR devices that are suitably large to resonate the whole body of the subject at one time (e.g., a whole body immersion device). Alternatively, certain MR devices 110 may be local area MR devices, meaning MR devices that are sized to resonate local areas only of body of the subject (e.g., a partial immersion device).

Thus, embodiments of the MR device 110 are capable of producing an electromagnetic field with a variety of flux density ranges, including, for example, the range of about 1 gauss to about $10^{-50}$ gauss, or ranges within this range. In some embodiments, this range encompasses the capacity to treat a broad range of indications, illnesses, pathologies, and/or injuries. The indications that such a range may treat include, but are not limited to, genetic disorders, infectious RNA and DNA immunogenic conditions, viral disorders, autoimmune disorders, disorders caused by or concomitant to infection by haptens, prions and the like, fungal and bacterial disorders, disorders of the nervous system (CNS and PNS), autonomic nervous system disorders, cardiovascular, neurological, endocrinological, circulatory and lymphatic disorders, immunological disorders, physical trauma, cancer, AIDS, Parkinson's disease, Alzheimer's disease, multiple sclerosis, amyotrophic lateral sclerosis, diabetes, cardiac arrhythmias, sports injuries, muscular dystrophy, attention deficit disorder, attention deficit hyperactive disorder, cerebral palsy, and others.

Flux density ranges may be viewed as windows of opportunity. In various embodiments, beneficial flux ranges are to be found within the broad range of 1 gauss to about $10^{-50}$ gauss. For example, about $10^{-5}$ gauss to about $10^{-12}$ gauss is a range wherein various oncogenic, and/or immunogenic transmissible disorders such as AIDS and cancer may be treated successfully. This range also may prove effective in treating autoimmune disorders, e.g., osteoarthritis and diabetes mellitus type II. This range may also prove effective in treating neurological disorders, e.g. Parkinson's, Alzheimer's, multiple sclerosis and LS. This range may also prove effective in treating cardiovascular disorders, e.g., cardiac arrhythmogenic disorders such as tachycardia, actual fibrillation, ventricular fibrillation and the like. This range may also prove effective in treating neuromuscular disorders, e.g., muscular dystrophy. This range may also prove effective in treating psychological/brain disorders, e.g., depression and schizophrenia. This range may also prove effective in treating sports injuries, e.g., sprains, strains, tendonitis, rotator-cuff injuries, hamstring injuries and the like and many others.

In some embodiments, geomagnetic field flux densities within the range of about 0.3 gauss to about 0.7 gauss may be utilized to improve circulatory disorders, alleviation of pain, bone healing, and others. In further embodiments, ranges such as $4\times10^{-7}$ gauss to about $5.5\times10^{-7}$ gauss may be utilized to treat such conditions as diabetic neuropathy. Also, ranges from about $3\times10^{-7}$ gauss to about $4.6\times10^{-7}$ gauss may be utilized to treat such conditions as fibromyalgia, chronic fatigue syndrome. In some embodiments, such ranges as $3\times10^{-8}$ gauss to about $4.8\times10^{-7}$ gauss may be utilized to treat such conditions as osteoarthritis, bone-nonunions and the like. Further, ranges such as $10^{-5}$ gauss to about $10^{-20}$ gauss may be utilized to treat such conditions as cancer, including but not limited to, breast cancer, prostrate cancer, leukemia, lymphoma lung cancer, brain tumors, pancreatic cancer, stomach cancer, rectal cancer. Additionally, ranges from $10^{-20}$ gauss to $10^{50}$ gauss may be utilized to treat terminal cancer (full body metastasis) including but not limited to, lung cancer, brain cancer, pancreatic cancer, autoimmune disorders and others.

Further, such ranges as $10^4$ gauss to about $10^{-9}$ gauss may be utilized to treat various conditions such as severe pain from burns. Also, such ranges as $6\times10^{-8}$ gauss to about $8\times10^{-8}$ may be utilized to treat neurological conditions such as depression, cerebral palsy, schizophrenia, Parkinson's, Alzheimer's, and others. In further embodiments, such ranges as $6.6\times10^{-8}$ gauss to about $7.8\times10^{-8}$ gauss may be utilized to treat such neurological conditions as Parkinson's disease, Alzheimer's, and depression. Also, such ranges as $5\times10^{-7}$ gauss to about $1\times10^{-8}$ gauss may be used to treat such conditions as diabetes types I and II. Additionally, such ranges as $2\times10^{-8}$ gauss to about $3.3\times10^{-8}$ gauss may be used to treat such conditions as migraine headache and cardiac arrhythmias.

In additional embodiments, the MR device is capable of producing a frequency in a variety of ranges. These ranges may include a broad range of 0 Hz to about 1,000 Hz.

In some embodiments, correspondent frequencies to flux densities, utilizing, for example, the apparatus, may include a variety of example ranges of opportunity. One example range of opportunity includes, but is not limited to, about 0 Hz to 1 Hz. This range maybe utilized to treat a variety of indications including, but not limited to, headache, cardiac arrhythmias and soft tissue injuries.

In some embodiments, the frequency range from about 1.8 Hz to about 7.8 Hz is used to treat one or more neurological disorders. These neurological disorders may include one or more of Parkinson's disease or depression. In some embodiments, the frequency range of 0 Hz to 140 Hz is used to treat one or more neurological disorders. The neurological disorders treated by this range may include Parkinson's disease. For example, this range may treat a Parkinson's disease patient for one or more of tremor, rigidity or dyskinesias.

In some embodiments, the frequency range from about 0 Hz to about 16 Hz can be used to treat conditions such as, for example, one or more of: osteoarthritis, neuropathy, fibromyalgia, muscular dystrophy, attention deficit disorder, autism, Alzheimer's disease, muscular sclerosis, cancer or viral disorders.

Additionally, multiple frequencies may be utilized with specified flux densities. For example, a flux density of $7.5\times10^{-8}$ gauss may be utilized with frequencies of about 2.1 Hz, 5 Hz, 5.3 Hz, and 7.5 Hz, and/or others. Also, a flux density of $7.7\times10^{-8}$ gauss may be utilized with frequencies of 2.156 Hz and 5.6 Hz, and/or others. Additionally, a frequency range from about 13.992 Hz to about 14.2 Hz may be used to treat diabetic neuropathy in accordance with a flux density range of about $4.992\times10^{-7}$ gauss to about $5.2\times10^{-7}$ gauss. Protonic frequencies ranging from 0 Hz to about 0.043 Hz may be used to treat cardiac arrhythmias in conjunction with a flux density of about $2.86\times10^{-6}$ gauss. In further embodiments, a frequency range of 0 Hz to about 130 Hz may be used to treat a wide variety of disorders, e.g. cancer, neurological disorders, bone disorders, endocrine disorders, immune disorders, skin disorders, GI disorders, metabolic disorders (lipid and carbohydrate), and/or others.

In one embodiment, each MR device 110 may be the whole body MR device that is described with reference to U.S. patent application Ser. No. 12/546,385, entitled "Systems and Methods for Providing a Magnetic Resonance Treatment to a Subject," and is herein incorporated by reference. U.S. patent application Ser. No. 12/546,385 describes an apparatus and system for programmable, precise, low-level magnetic resonance (MR). In some embodiments, the MR system includes a coil assembly. In some embodiments, the MR system includes one or more sensors. In some embodiments, the MR system includes a coil housing. In some embodiments, the MR system includes a compensation network. In some embodiments, the MR system includes a magnetometer. In some embodiments, the MR system includes an MR driver. In some embodiments, the MR system includes a personal computer. In some embodiments, the MR system includes a signal generator. In some embodiments, the MR system includes one or more latching relay devices. In some embodiments, the MR system includes a voltage reference device. In some embodiments, the MR system includes one or more digital-to-analog converters. In some embodiments, the MR system includes a differential amplifier. In some embodiments, the MR system includes a temperature sensing device. In some embodiments, the MR system includes an attenuator. In some embodiments, the MR system includes a dummy load. In some embodiments, the MR system includes a microcontroller and software. In some embodiments, the MR system includes a system bus. In some embodiments, the MR system includes a power supply. The signal generator may provide any waveform, such as any sinusoidal wave, any non-sinusoidal wave, and/or any combination thereof. Examples of non-sinusoidal waveforms include, but are not limited to, square waves, rectangular waves, ramp waves, triangle waves, spiked waves, rectilinear waves, and sawtooth waves.

A method of operating an embodiment of an MR system that may be used with the present invention, such as the system described in U.S. patent application Ser. No. 12/546,385 may include one or more of the following steps: applying power to the display, entering operational commands and therapeutic parameters, providing inputs to the MR driver, reading the magnetometer and other sensors, computing required signals, driving the coil assembly, measuring results, indicating results, changing settings, and powering down the system. More details of an example of a whole body MR device according to one embodiment are described in more detail below with reference to FIG. 2.

In some embodiments, and still referring to FIG. 1, the one or more client computers 120 that are associated with each MR device 110 may be any standard computing device, such as any desktop, laptop, or handheld computer, that is capable of executing program instructions and of connecting to a network. Additionally, each client computer 120 may include one or more standard computer components, such as, but not limited to, one or more of: a processor 122, a set of input/output (I/O) devices 124, a network interface 126, and a storage device 128.

In some embodiments, the client computers 120 are used by one or more operators 138 that are associated with the MR devices 110. Each operator 138 may be the responsible party for operating each respective MR device 110. The operator may operate the MR device 100 via the corresponding client computer 120. Operators 138 may include, for example, practitioners, research personnel, and/or any individual who is capable of operating an MR device 110. In some embodiments, one individual may be both the subject and the operator. In other words, a certain subject may also be the operator of the MR device 110 by which he/she is receiving treatment.

In some embodiments, the processor 122 may be any central processing unit (CPU), controller, or microcontroller device that is capable of managing the overall operations of the one or more client computers 120. Examples of tasks performed by the processor 122 in various embodiments include one or more of: managing I/O devices, network communication, data exchange and storage, and executing the program instructions of any software applications that may be loaded on the one or more client computers 120.

In some embodiments, the one or more I/O devices 124 may include one or more of: a display device, a keyboard, a touch screen, mouse, speaker, and/or printer. In some embodiments, the network interface 126 may be any standard wired (USB or Ethernet connection) and/or wireless (e.g., IEEE 802.11 and/or Bluetooth® technology) communications link for connecting to a network, such as network 140. The network 140 may be, for example, a wide area network (WAN), a local area network (LAN), a wireless network, a public telephone network, an intranet, the Internet, and/or any known communication means.

In some embodiments, the storage device 128 may be, for example, any volatile or non-volatile data storage mechanism, such as, but not limited to, a random access memory (RAM) or other dynamic storage device, a computer hard drive, a floppy disk drive, and any combinations thereof.

In some embodiments, an instance of MR device software 130 also resides on each client computer 120. The MR device software 130 may be the device-specific control software of MR device 110. For example, in one embodiment, MR device software 130 provides the ability to manage the operational settings of MR device 110, such as but not limited to, one or more of: the flux density, frequency, amplitude, waveform shape, and duration of the electromagnetic energy that is supplied by MR device 110. A user interface 132 may be, for example, the device-specific graphical user interface (GUI) that is associated with the MR device 110 and MR device software 130. The device-specific GUI (not shown) may be displayed to the user via the display of the one or more client computers 120.

In some embodiments, one or more of the subject data 134, MR device data 136, and treatment data 137 are associated with MR device 110 and MR device software 130. The data may be stored upon the storage device 128. Subject data 134 may be user-specific data of, for example, one or more subjects 150 of MR system 100. Subjects 150 may be individuals who are receiving magnetic resonance via MR devices 110 before, concomitant with, or after one or more substances 152 for treating a certain indication have been introduced to their body. While in the context of this description, subjects 150 may refer to humans, those skilled in the art will recognize that subjects 150 may represent any living systems, such as any living animals, plants, and/or humans, that may receive the magnetic resonance treatment by use of MR system 100 of the invention.

The substances 152 may be, for example, ingestible substances, injectable substances, topically-applied substances, and any combinations thereof. In particular, the substances 152 may include one or more beneficial substances. In certain embodiments, the substance may include water and/or other beverages, foods, nutraceuticals, pharmaceuticals, drugs, and the like.

Embodiments of the present invention may comprise a substance (e.g., a beneficial substance) mixed with a pharmaceutically acceptable carrier. Pharmaceutically acceptable carriers may comprise any of the standard pharmaceutically accepted carriers known in the art. In one embodiment, the pharmaceutical carrier may be a liquid and the substance to be administered may be in the form of a solution. In other embodiments, the pharmaceutically acceptable carrier may be a solid in the form of a powder, a lyophilized powder, or a tablet. Or, the pharmaceutical carrier may be a gel, suppository, or cream. In alternate embodiments, the carrier may comprise a liposome, a microcapsule, a polymer encapsulated cell, or a virus. Thus, the term pharmaceutically acceptable carrier encompasses, but is not limited to, any of the standard pharmaceutically accepted carriers, such as water, alcohols, phosphate buffered saline solution, sugars (e.g., sucrose or mannitol), oils or emulsions such as oil/water emulsions or a trigyceride emulsion, various types of wetting agents, tablets, coated tablets and capsules.

Administration of the substance may employ various routes. Administration of the substance may employ a parenteral route. For example, administration of the substance may employ a carrier suitable for intraperitoneal (IP) injection. In another embodiment, administration is intravenous (IV). The substance may also be injected subcutaneously. Alternatively, the substance may be administered orally, intranasally, or as an aerosol and thus, may comprise a carrier suitable for oral, intranasal or aerosol administration. In another embodiment, administration of the substance is intra-arterial. In another embodiment, administration is sublingual. Also, administration may employ a time-release capsule. In these embodiments, the carrier may be suitable for IV, intraarterial, subcutaneous, sublingual, or time-release administration. For example, subcutaneous administration may be useful to treat chronic disorders when self-administration is desirable.

The substance may, in some embodiments, be in the form of a sterile injectable solution in a non-toxic parenterally acceptable solvent or vehicle. Among the acceptable vehicles and solvents that may be employed are water, Ringer's solution, 3-butanediol, isotonic sodium chloride solution, or aqueous buffers, as for example, physiologically acceptable citrate, acetate, glycine, histidine, phosphate, tris or succinate buffers. The injectable solution may contain stabilizers to protect against chemical degradation and aggregate formation. Stabilizers may include antioxidants such as butylated hydroxy anisole (BHA), and butylated hydroxy toluene (BHT), buffers (citrates, glycine, histidine) or surfactants (polysorbate 80, poloxamers). The solution may also contain antimicrobial preservatives, such as benzyl alcohol and parabens. The solution may also contain surfactants to reduce aggregation, such as Polysorbate 80, poloxomer, or other surfactants known in the art. The solution may also contain other additives, such as a sugar(s) or saline, to adjust the osmotic pressure of the composition to be similar to human blood.

The substance may, in some embodiments, be in the form of a sterile lyophilized powder for injection upon reconstitution with a diluent. The diluent can be water for injection, bacteriostatic water for injection, or sterile saline. The lyophilized powder may be produced by freeze drying a solution of the fusion protein to produce the protein in dry form. As is known in the art, the lyophilized substance may have increased stability and a longer shelf life than a liquid solution of the protein. The lyophilized powder (cake) many contain a buffer to adjust the pH, as for example physiologically acceptable citrate, acetate, glycine, histidine, phosphate, tris or succinate buffer. The lyophilized powder may also contain lyoprotectants to maintain its physical and chemical stability. Commonly used lyoprotectants are non-reducing sugars and disaccharides such as sucrose, mannitol, or trehalose. The lyophilized powder may contain stabilizers to protect against chemical degradation and aggregate formation. Stabilizers may include, but are not limited to antioxidants (BHA, BHT), buffers (citrates, glycine, histidine), or surfactants (polysorbate 80, poloxamers). The lyophilized powder may also contain antimicrobial preservatives, such as benzyl alcohol and parabens. The lyophilized powder may also contain surfactants to reduce aggregation, such as, but not limited to, Polysorbate 80 and poloxomer. The lyophilized powder may also contain additives (e.g., sugars or saline) to adjust the osmotic pressure to be similar to human blood upon reconstitution of the powder. The lyophilized powder may also contain bulking agents, such as sugars and disaccharides.

The substance to be administered may also be in the form of an oleaginous suspension. This suspension may be formulated according to the known methods using suitable dispersing or wetting agents and suspending agents described above. In addition, sterile, fixed oils may be employed as solvent or suspending medium. For this purpose, any bland fixed oil may be employed using synthetic mono- or diglycerides. Also, oily suspensions may be formulated by suspending the active ingredient in a vegetable oil, for example arachis oil, olive oil, sesame oil or coconut oil, or in a mineral oil such as a liquid paraffin. For example, fatty acids such as oleic acid find use in the preparation of injectables. The oily suspensions may contain a thickening agent, for example beeswax, hard paraffin or cetyl alcohol. These compositions may be preserved by the addition of an anti-oxidant such as ascorbic acid.

The substances to be administered may also be in the form of oil-in-water emulsions or aqueous suspensions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan.

Aqueous suspensions may also contain the substance to be administered in admixture with excipients. Such excipients may include suspending agents, for example sodium carboxymethylcellulose, methylcellulose, hydroxypropylmethylcellulose, sodium alginate, polyvinylpyrrolidone, gum tragacanth and gum acacia; dispersing or wetting agents, such as a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate.

Dispersible powders and granules suitable for preparation of an aqueous suspension by the addition of water may provide the substance to be administered in admixture with a dispersing agent, suspending agent, and one or more preservatives. Suitable preservatives, dispersing agents, and suspending agents are described above.

The substance to be administered may also be in the form of a suppository for rectal administration. These compositions can be prepared by mixing the substance with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions or suspensions containing the substance to be administered may be used. Topical applications may also include mouthwashes and gargles. Suitable preservatives, antioxidants such as BHA and BHT, dispersants, surfactants, or buffers may be used.

The substance may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

In certain embodiments, the substance to be administered may be modified to further retard clearance from the circulation by metabolic enzymes. In one embodiment, a compound or compounds in the beneficial substances may be modified by the covalent attachment of water-soluble polymers such as polyethylene glycol (PEG), copolymers of PEG and polypropylene glycol, polyvinylpyrrolidone or polyproline, carboxymethyl cellulose, dextran, polyvinyl alcohol, and the like. Such modifications also may increase the compound's solubility in aqueous solution.

Also, the substance to be administered may be utilized in adjuvant therapeutic or combination therapeutic treatments with other known therapeutic agents.

The substance may be administered as a therapeutically effective amount. As noted above, use of magnetic resonance may reduce the amount of the beneficial substance that is needed so as to be therapeutically effective. Also, the amount may vary with the subject being treated. Administration of the compound may be hourly, daily, weekly, monthly, yearly, or as a single event. Thus, as is known to those in the art, the effective amount may depend on bioavailability, bioactivity, and biodegradability of the compound.

In some embodiments, the subject data 134 may include one or more of: each user's demographic information (e.g., age, gender, ethnicity, address), health information (e.g., personal medical history, family medical history), lifestyle information (e.g., smoker or non-smoker), and MR history information (e.g., a record of prior MR treatments). The MR device data 136 may include, for example, a record of the operational settings of MR device 110 for each MR treatment of each subject 150. The treatment data 137 may include one or more of: date and time of treatment, type and dosage of substance 152 that is administered to each subject 150 during each MR treatment, substance interaction method, and results of each MR treatment.

In some embodiments, the one or more client computers 120 that are associated with the one or more MR devices 110 are in communication with a centralized server via the network 140. More specifically, the MR system 100 may include an MR system server 160. The MR system server 160 may include any centralized computer that is accessible by other computers (e.g., one or more client computers 120) via network 140 and that is capable of hosting certain applications that are likewise accessible via the network 140. In one embodiment, the MR system server 160 is a centralized server that stores, collates, and analyzes magnetic resonance treatment and subject-specific data in order to generate an actionable magnetic resonance treatment recommendation.

In one embodiment, the MR system server 160 includes an MR application 162. The MR application 162 may further include an MR web application 164 and/or an MR analysis algorithm 166. In some embodiments, an MR database 168 also resides on MR system server 160. Stored on MR database 168 may be a collection of any data that is related to MR system 100, such as, but not limited to, one or more of: aggregate subject data 170, aggregate MR device data 172, aggregate treatment data 174, and one or more MR reference tables 176.

The MR application 162 may be, for example, a custom application for managing the overall operations of MR system 100. In some embodiments, the MR application 162 manages the operations to store, collate, and analyze magnetic resonance treatment and subject-specific data in order to generate an actionable magnetic resonance treatment recommendation. The MR application 162 of MR system server 160 may also be used to distribute any system data and/or software updates to the one or more authorized client computers 120 that are connected to network 140.

Additionally, in some embodiments, the MR application 162 facilitates the use of the MR system 100. In various embodiments, the MR system 100 may be used by one or more of: any authorized system administrator, authorized users of the one or more MR devices 110, and/or authorized operators 138 (e.g., practitioners) of the one or more MR devices 110. That is, MR application 162 may handle the security and authentication function for MR system 100 using standard security and authentication methods. The MR web application 164 of MR application 162 may be, for example, a custom web application for accessing and using MR application 162 of MR system server 160 from a remote location, such as from any authorized client computers 120. Additionally, by use of the MR analysis algorithm 166, the MR application 162 is able to query and analyze information that resides on the MR database 168 for information that may be used to develop a magnetic resonance treatment regimen for a certain user, substance, and indication. More details of an example method of generating a magnetic resonance treatment regimen using an MR application and an MR database for improving the efficacy of a substance before, concomitant with, or after being administered to the subject are described with reference to FIGS. 3 and 4, herein.

The MR database 168 may be created and maintained by any suitable database software, such as Oracle database software from Oracle Corporation (Redwood Shores, Calif.). In some embodiments, the MR database 168 stores relationships between, for example, unique user information, substance information, MR device information, and/or information about certain indications. The contents of the MR database 168 may be organized in any user-defined relational database structure.

The aggregate subject data 170 may be a collection of all subject data 134 (e.g., user-specific data of subjects 150) from one or more authorized client computers 120 of the MR system 100. The aggregate subject data 170 may be compiled from the subject data 134 that is transmitted from all client computers 120. The subject data 134 may be transmitted to the MR system server 160 via the network 140. The aggregate subject data 170 may be updated in an ongoing fashion as new or updated subject data 134 is received.

Still referring to FIG. 1, in some embodiments, the aggregate MR device data 172 is a collection of all MR device data 136 (e.g., MR device-specific data of MR devices 110) from one or more authorized client computers 120 of the MR system 100. The aggregate MR device data 172 may be compiled from MR device data 136 that is transmitted from all client computers 120. The MR device data 136 may be transmitted to the MR system server 160 via the network 140. The aggregate MR device data 172 may be updated in an ongoing fashion as new or updated MR device data 136 is received. In some embodiments, the MR device data 136 also includes the device type and model used during the MR session.

The aggregate treatment data 174 may be a collection of all treatment data 137 from one or more authorized client computers 120 of the MR system 100. The aggregate treatment data 174 may be compiled from treatment data 137 that is transmitted from all client computers 120 to the MR system server 160 via the network 140. The aggregate treatment data 174 may be updated in an ongoing fashion as new or updated treatment data 137 is received.

Additionally, the aggregate treatment data 174 may include a compilation of substance-specific data of, for example, the various types of substances 152 that may be used within MR system 100. For example, the substance-specific data may be supplied by the supplier and/or manufacture of certain substances 152, such as water and/or other beverages, foods, nutraceuticals, pharmaceuticals, drugs, and the like. The substance-specific data of the aggregate treatment data 174 may be supplied from one or more third party servers 180. For example, the substance-specific data 184 may be transmitted from one or more third party servers 180 to the MR system server 160 via the network 140. The substance-specific data 184 may include, for example, the ingredients, chemical formulations, and/or nutritional information that are related to one or more substances 152. The substance-specific data 184 may be updated in an ongoing fashion as new or updated information is received.

In some embodiments, the MR reference or lookup tables 176 comprise a collection of empirical data that may be compiled over time. The MR reference tables 176 may contain a record of one or more magnetic resonance treatment regimens and associated results that have been performed by use of MR system 100. In one embodiment, the MR reference tables 176 may contain a record of all of the magnetic resonance treatment regimens and associated results that have been performed by use of MR system 100. The MR reference tables 176 may include information from one or more of: the aggregate subject data 170, the aggregate MR device data 172, and the aggregate treatment data 174. In one embodiment, the information in the MR reference tables 176 is organized in an easily searchable fashion in order to accommodate the search and analysis operations of the MR analysis algorithm 166. While the information within the MR reference tables 176 may include empirical data that is compiled from one or more of the aggregate subject data 170, the aggregate MR device data 172, and the aggregate treatment data 174, the MR reference tables 176 may also include data that is derived from other sources. In one embodiment, the MR reference tables 176 include data that is scientifically derived. More details of example records that may be contained in MR reference tables 176 are shown in Table 1.

In one embodiment, the aggregate subject data 170, aggregate MR device data 172, and aggregate treatment data 174 are organized relationally to certain indications of interest along with their corresponding device type/model. For example, when the indication of interest is Parkinson's disease, the MR reference tables 176 may be organized to allow the MR analysis algorithm 166 to easily extract any and all records that relate to magnetic resonance treatment events that have occurred upon magnetic resonance of certain substances and subjects for the purpose of treating Parkinson's disease, wherein the treatments occur after the substances have been administered to the bodies of the subjects. Once the data of interest had been extracted, the MR analysis algorithm 166 performs an analysis for comparing this subset of magnetic resonance treatment events to the scenario of an upcoming magnetic resonance treatment event. In this way, the MR application 162 and/or MR analysis algorithm 166 may generate a recommended magnetic resonance treatment regimen that is most likely to be successful for the certain scenario of interest.

In one embodiment, the MR analysis algorithm 166 may query the MR database 168 and categorize records using a quantitative analysis. For example, the criterion may be categorized as a BEST match, GOOD match, POOR match, and NO match against the subject data 134 of the subject 150 of interest. Furthermore, the categorization may vary from indication to indication, i.e., the criteria for categorizing the records may be indication-specific. More details of an example of a method of generating a recommended treatment regimen are described with reference to FIG. 4.

Table 1 below shows an example of records that may be contained in the MR reference tables 176. In particular, Table 1 shows a subset of records that may be the result of an analysis that is performed by the MR analysis algorithm 166. In the example of Table 1, the MR analysis algorithm 166 has performed a query, for example, on the terms "Indication=Parkinson's" in combination with "Substance=Levodopa," in order to produce one or more records of one or more subjects of one or more treatment events.

In one embodiment, once a subset of records of interest are identified, the MR analysis algorithm 166 may determine which record or records completely match and/or most closely match the circumstance of a certain subject 150 that is about to receive a treatment via a certain MR device 110. In this way, the MR analysis algorithm 166 may be used to generate a recommended magnetic resonance treatment regimen that may be transmitted to a certain client computer 120 for execution thereof.

TABLE 1

Example records of MR reference tables 176

| Subject Data | | MR device data | | Treatment data | |
|---|---|---|---|---|---|
| Record # 1265 | | | | | |
| Subject ID | A-84 | Device type | Whole body immersion (7') | Date | Jan. 24, 2007 |
| Indication | Parkinson's | Amplitude | 0.0667 microgauss | Start Time | 10:47 AM |
| Sex | F | Frequency | 2.0 Hz | Substance | Levodopa |
| Race | Asian | Waveform | Square | Dosage | 25 mg |
| Age | 59 | Duration | 60 mins | Dosage Time | 10:45 AM |
| Height | 61 inches | | | Interaction | Ingested |
| Weight | 110 lbs | | | Baseline | Onset of Dyskinesias 38 mins |

TABLE 1-continued

Example records of MR reference tables 176

| Subject Data | | MR device data | | Treatment data | |
|---|---|---|---|---|---|
| Other | Smoker | | | MR Result | Onset of Dyskinesias 22 mins |
| | | | | % Improved | 42% |
| | | | | Treatment Protocol # | 101 |
| | | | Record # 4752 | | |
| Subject ID | W-65 | Device type | Partial immersion (4') | Date | Mar. 3, 2007 |
| Indication | Parkinson's | Amplitude | 0.0697 microgauss | Start Time | 8:15 AM |
| Sex | M | Frequency | 1.9 Hz | Substance | Levodopa |
| Race | White | Waveform | Sinusoidal | Dosage | 50 mg |
| Age | 47 | Duration | 90 mins | Dosage Time | 8:00 AM |
| Height | 70 inches | | | Interaction | Ingested |
| Weight | 210 lbs | | | Baseline | Average off time 6 hours |
| Other | Non-Smoker | | | MR Result | Average off time 5 hours |
| | | | | % Improved | 17% |
| | | | | Treatment Protocol # | 102 |
| | | | Record # 5942 | | |
| Subject ID | AA-35 | Device type | Partial immersion (22") | Date | Nov. 11, 2007 |
| Indication | Parkinson's | Amplitude | 0.0717 microgauss | Start Time | 2:23 PM |
| Sex | F | Frequency | 1.8 Hz | Substance | Levodopa |
| Race | African Amer | Waveform | Triangle | Dosage | 25 mg |
| Age | 63 | Duration | 70 mins | Dosage Time | 2:30 PM |
| Height | 65 inches | | | Interaction | Ingested |
| Weight | 135 | | | Baseline | Average off time 6 hours |
| Other | Non-Smoker | | | MR Result | Average off time 4 hours |
| | | | | % Improved | 33% |
| | | | | Treatment Protocol # | 103 |
| | | | Record # 7508 | | |
| Subject ID | W-65 | Device type | Whole body immersion (7') | Date | Feb. 20, 2008 |
| Indication | Parkinson's | Amplitude | 0.0697 microgauss | Start Time | 10:25 AM |
| Sex | M | Frequency | 1.9 Hz | Substance | Levodopa |
| Race | White | Waveform | Sinusoidal | Dosage | 50 mg |
| Age | 47 | Duration | 80 mins | Dosage Time | 10:20 AM |
| Height | 68 inches | | | Interaction | Ingested |
| Weight | 175 lbs | | | Baseline | Onset of Dyskinesias 43 mins |
| Other | Smoker | | | MR Result | Onset of Dyskinesias 27 mins |
| | | | | % Improved | 37% |
| | | | | Treatment Protocol # | 104 |

Table 1 is exemplary only. While one record only is shown for each different subject ID, in various embodiments multiple records for each subject ID may exist. For example, one record may correspond to one treatment event using the MR system of the invention. Additionally, while the contents of Table 1 are specific to the Parkinson's patients example, the contents of Table 1 may be tailored for any indication and/or condition and for any set of subject data, MR device data, and/or treatment data. For example, the MR device data may include data from the various sensors of the MR devices 110.

Figure 2:
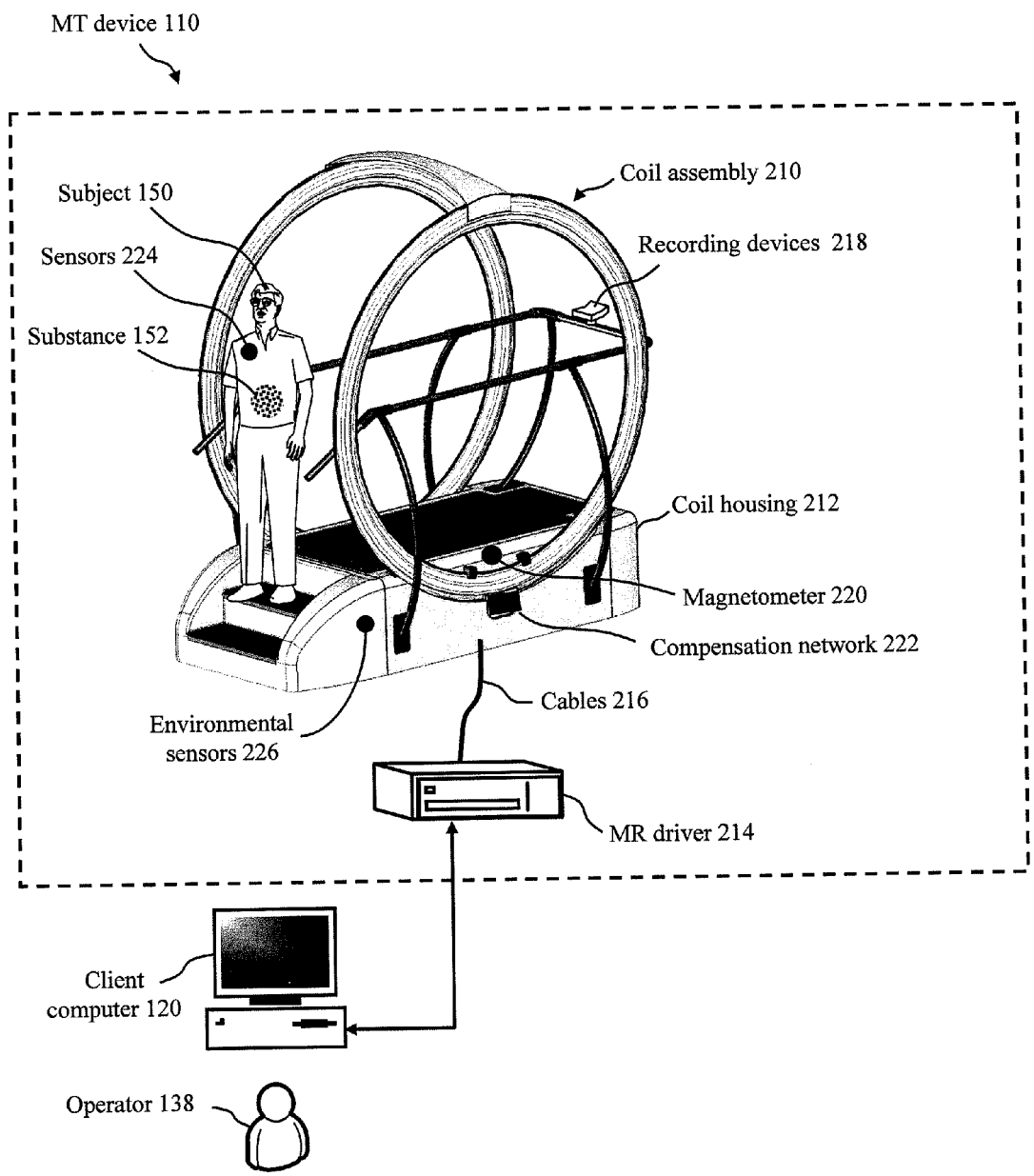
FIG. 2 illustrates a perspective view of an example of a magnetic resonance device that is suitable for use with the magnetic resonance system, according to one embodiment of the invention.

FIG. 2 illustrates a perspective view of an example of a magnetic resonance device that is suitable for use with the magnetic resonance system, according to one embodiment of the invention. In one embodiment, the MR device 110 of FIG. 2 is the MR device that is described with reference to U.S. patent application Ser. No. 12/546,385 and that is summarized as follows.

In some embodiments, the MR device 110 may include a coil assembly 210. The coil assembly 210 may be mounted on a coil housing 212. In some embodiments, the coil assembly 210 and coil housing 212 are driven by a separate MR driver 214. The MR driver 214 may be electrically connected to the coil housing 212. The MR driver 214 may be connected to the coil housing 212 via one or more cables 216. One or more recording devices 218 may be mounted upon the coil assembly 210. Some embodiments include a magnetometer 220. Some embodiments include a compensation network 222. In some embodiments, the magnetometer 220 and/or the compensation network 222 are mounted upon the coil housing 212. Additionally, FIG. 2 shows a subject 150 that is receiving magnetic treatment via the MR device 110, where a certain substance 152 has been introduced to the body of the subject 150 prior to the subject 150 receiving the magnetic resonance treatment. In some embodiments, one or more sensors 224 are attached to the subject 150 while receiving the magnetic resonance treatment. Some embodiments include one or more environmental sensors 226. The one or more environmental sensors 226 may be mounted upon the coil housing 212. Further, in some embodiments, a client computer 120, which is described in FIG. 1, may be in communication with the MR driver 214 via a wired or wireless connection.

The coil assembly 210 may be any magnetic coil configuration that produces a uniform magnetic field over a specified area of sufficient volume to accommodate a magnetic resonance subject, such at the subject 150. In one embodiment, the coil assembly 210 is a Helmholtz coil that includes two co-axial coils that have a diameter of about 7 feet and that may be spaced about 3.5 feet apart. In one embodiment, each coil of coil assembly 210 may have about 30 turns of about 30-gauge solid-core copper wire. However, other coil configurations of other dimensions, turns, and construction (e.g., 4-coil or 6-coil designs) are possible in accordance with the invention, such as the coil configurations described in U.S. patent application Ser. No. 12/546,385, entitled "Systems and Methods for Providing a Magnetic Resonance Treatment to a Subject," incorporated by reference herein. Examples of other types of coils that may be suitable for use in coil assembly 210 include poloidal coils, Maxwell coils, and solenoids. In one embodiment, the coil assembly 210 is wired in parallel with the compensation network 222. Further, the coil assembly 210 may be electrically connected to the MR driver 214. In one embodiment, the coil assembly 210 is wired in parallel with the compensation network 222. Further, the coil assembly 210 and/or the compensation network 222 may be housed within the chassis of coil housing 212. Alternatively, the coil assembly 210 may be sized according to the type of MR device (e.g., whole body immersion or body part immersion device).

In some embodiments, the coil housing 212 is a chassis that provides a mounting pedestal and/or enclosure for the coil assembly 210 and one or more of the other components of the MR device 110 as shown. Additionally, the coil housing 212 may provide a platform for subjects receiving magnetic resonance to position themselves within the coil assembly 210. The coil housing 212 may be constructed of a non-magnetic and non-conductive housing, such as fiberglass or composite, in order to minimize magnetic interference with coil assembly 210. The coil housing 212 may be of a variety of sizes and shapes (i.e., form factors) that are capable of accommodating different sized and shaped coil assemblies 210. In addition, the coil housing 212 may also provide a means of easily changing the position and orientation of the coil assembly 210. For example, the coil housing 212 may include an articulated mechanical arm for use with smaller coils.

In some embodiments, the MR driver 214 is a custom low-level electronic waveform generator, for use in MR device 110. In operation, according to one embodiment, one or more of the one or more client computers 120 communicates operational commands, such as normal operation on/off, AC calibration, and DC calibration to the MR driver 214. For normal operation, the client computer 120 may communicate specific magnetic waveform parameters, such as waveform type (e.g., sinusoidal, square, sawtooth), amplitude (e.g., 1 millivolt, 0.032 micro-gauss, 0.017 micro-gauss, 0.075 micro-gauss) and frequency (e.g., 0.3 Hz, 0.8 Hz, 5 Hz, 10 Hz) to the MR driver 214. Further, in one embodiment, the MR driver 214 possesses shielding elements (not shown) that reduce, preferably entirely prevent, electromagnetic radiation that emanates from MR driver 214 from interfering with the operation of MR device 110. For example, a chassis exterior shield of about 20 thousandths inches (0.02") steel or about 10 thousandths inches (0.01") mu metal may be provided.

In some embodiments, the one or more cables 216 between the MR driver 214 and the coil housing 212 may include a set of coil cables. The coil cables may be short electrical cables that have connectors that provide an analog signal that powers the coil assembly 210. The cable 216 may be such that it enables the coil assembly 210 to produce the specific magnetic waveform (e.g., magnitude and frequency) that is required for performing magnetic resonance.

In one embodiment, the coil cables include a shielded twisted pair that has a 156 Molex connector. Additionally, the cables 216 may include a magnetometer cable that provides a standard digital serial communication means, for example, USB or RS232. The magnetometer cable may enable the communication of magnetic field data between the magnetometer 220 and the MR driver 214. In some embodiments, the magnetometer cable provides power and ground to the magnetometer 220. In one embodiment, the MR driver 214 is located in close proximity to the coil assembly 210, thereby minimizing the length of the cables 216 and, therefore, minimizing electrical noise.

In some embodiments, the magnetometer 220 is a magnetic sensor that measures the magnetic field between the coils of the coil assembly 210. The magnetometer 220 may be capable of measuring low-level magnetic fields, such as in the nano-Tesla (nT) range (i.e. 0.1 nT to 100 nT, at 5-10%), and of resolving the magnitude of these fields into three orthogonal components (x-y-z). An example of a magnetometer 220 is the GSMP-20GS magnetic field measuring device that may be supplied, for example, by Terraplus Inc. (Ontario, Canada). The GSMP-20GS device is a highly sensitive proton precession gradiometer with two aligned sensors, which has an RMS resolution of about 0.05 pT. Another example of a magnetometer 220 is the MAG-01H that may be supplied, for example, by Ecoseal Developments Pty Ltd (NSW, Australia). The MAG-01H device is a single-axis fluxgate magnetometer that has a resolution of about 0.1 nT. The use of the magnetometer 220 allows the MR driver 214 to sense the ambient magnetic environment and adapt its output to account for this field.

In some embodiments, the compensation network 222 may be a resistor and capacitor network that is matched to the impedance of coil assembly 210. The compensation network 222 may be used to negate the reactance of the coil over a small range of frequencies, for example, from about 0.1 Hertz to about 500 Hertz.

In some embodiments, the one or more recording devices 218 include devices such as video cameras, voice recorders, and/or motion capture devices. The sensors 224 may include, for example, a blood pressure sensor, a perspiration sensor, and/or a body weight sensor, among others. Additionally, the sensors 224 may include sensors that relate specifically to the subject's indication or condition. For example, a patient with Parkinson's disease may employ a haptics glove sensor in order to measure the subject's tremor severity, range of movement, speed of movement, finger fractionation, and/or strength of movement. Furthermore, the environmental sensors 226 may include sensors that are used, for example, to record air quality, humidity, oxygen level, barometric pressure, light intensity, and/or sound. Also, the sensors may include sensors that can monitor the level of a compound of interest within the cells, tissues, or organs of the subject.

In some embodiments, the one or more recording devices 218, sensors 224, and/or environmental sensors 226 may be connected to the MR driver 214 via one or more wired (e.g., USB and RS232) and/or wireless connections (e.g., IEEE 802.11 and Bluetooth).

If the client computer 120 is in physical proximity to the MR device 110, it may be beneficial to shield the client computer 120. The shielding elements (not shown) may reduce, preferably entirely prevent, electromagnetic radiation that emanates from the PC from interfering with the operation of the MR device 110. For example, a chassis exterior shield of about 20 thousandths inches (0.02") steel or about 10 thousandths inches (0.01") mu metal may be provided.

Referring to FIG. 2, in one embodiment, the client computer 120 is primarily used to perform one or more of the following tasks: (1) request and select treatment regimens from the MR system server 160, (2) capture and submit data related to treatment sessions to the MR system server 160, (3) add or update treatment protocol data to the MR system server 160, and (4) process system data and software updates from the MR system server 160.

In one embodiment, and referring to FIGS. 1 and 2, the operation of the MR system 100 may be summarized as follows. Using the client computer 120, the operator 138 may select a certain magnetic resonance treatment and initiate operation of the MR device 110 for a subject 150 that is suffering, for example, from Parkinson's disease in a hospital or clinical setting. Before starting the magnetic resonance treatment, using the client computer 120, the operator 138 may generate user-specific data (e.g., subject data 134) or, optionally, may access user-specific data of the subject from the aggregate subject data 170 of the MR system server 160 via the network 140 and display this information on the client computer 120. Additionally, the operator 138 may input additional subject-specific data from the subject being treated into the client computer 120. Finally, the operator 138 may obtain biometric, physiological, and observational data from the subject 150 using the sensors 224 and/or recording devices 218, respectively. The physiological and observational data may be captured and stored in the client computer 120.

Further to the example, if the subject 150 is a 42-year old, 150-pound, 5' 6" tall, Asian male that is taking Levodopa for Parkinson's disease, the MR analysis algorithm 166 may search the MR reference tables 176 for prior subject treatment records for that subject and/or one or more treatment records that are related to Parkinson's disease and to users that most closely match a 42-year old, 150-pound, 5' 6" tall, Asian male taking Levodopa for Parkinson's disease. Either before, concomitant with, or after the MR analysis algorithm 166 begins the search, the subject may be treated with a substance 152 as a treatment for Parkinson's disease. Once at least one substantially matching record of a like-situated subject is found, the MR application 162 and/or MR analysis algorithm 166 may generate a recommended magnetic resonance treatment regimen that is based upon the empirical and/or scientific data within the MR database 168. In one embodiment, and referring to Table 1, the MR analysis algorithm 166 may analyze the MR reference tables 176 of the MR database 168 and determine that "Record 7508" is a like-situated subject. As a result, the MR analysis algorithm 166 may recommend substantially the same treatment regimen that is logged in "Record 7508."

Subsequently, the selected magnetic resonance treatment regimen may be transmitted from the MR system server 160 to the client computer 120. The operator 138 then may carry out the treatment regimen upon the subject 150 according to the recommended treatment regimen. For example, the recommended magnetic resonance treatment regimen may specify a certain number and frequency of treatment events, wherein for each treatment an amount of a certain substance is administered to the body of the subject, and the subject is then resonated with electromagnetic energy of a certain flux density and certain frequency for a certain amount of time. Subsequent to each magnetic resonance treatment, all related data is updated locally at the client computer 120 and/or remotely at the MR system server 160. Using the example of a subject 150 that has Parkinson's disease, a side effect of certain Parkinson's drugs may be involuntary movements called dyskinesias. Therefore, an example of results that may be logged in treatment data 137 may be observations as to the amount of time from beginning of treatment to the onset of dyskinesias, which is an indication as to the amount of time that it has taken for the substance 152 to enter the subject's body systems. Other observable effects of the MR treatment after the substance 152 that has been administered to the subject's body systems may be a reduction in off time of the drug, a reduction in tremors, and a reduction in joint stiffness.

In another example, a subject 150 may operate the MR device 110 remotely without the need to interact with a certain operator 138. For example, a certain operator 138 may approve a recommended magnetic resonance treatment protocol that is generated at the MR system server 160 and advise the subject to receive this recommended treatment. The subject will have the flexibility of initiating and receiving this treatment by using the client computer 120 to operate the MR device 110 at his/her convenience.

Referring to FIGS. 1 and 2, those skilled in the art will recognize that an MR system, such as the MR system 100 of the invention, may also be considered an electro-gravitational system and/or an electromagnetic-gravitational system. Additionally, those skilled in the art will recognize that an MR device, such as the MR device 110 of the invention, may also be considered an electro-gravitational device and/or an electromagnetic-gravitational device.

Referring again to FIGS. 1 and 2, the MR device 110 provides a mechanism for magnetically resonating a certain substance 152 and the tissues, cells, molecules, and/or atoms of the subject before, concomitant with, or after the substance has been administered to (e.g., ingested, injected, applied topically, or transdermally) the body of a certain subject 150 that is subject of the magnetic resonance treatment. In doing so, the efficacy of the substance 152 for affecting a certain indication may be improved; the negative side effects of substance 152 on subject 150 may be reduced; and/or the quantity of substance 152 required to achieve the desired outcome on subject 150 may be reduced. The following examples provided herein demonstrate the effects of resonating a certain substance 152 and the tissues, cells, molecules, and/or atoms of subject 150 before, concomitant with, or after the substance has been administered to the body of a certain subject 150 that is subject of the magnetic resonance treatment.

Figure 3:
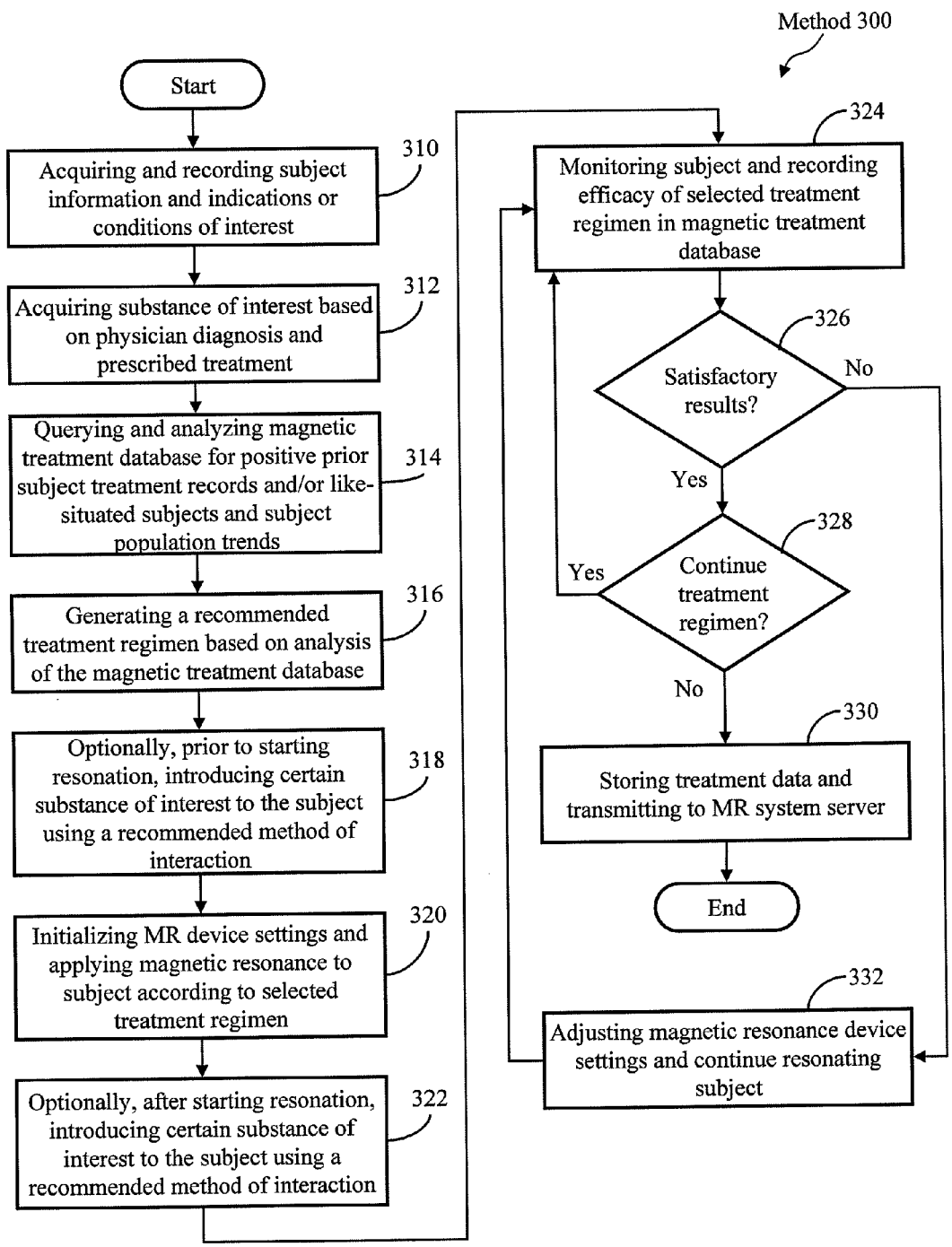
FIG. 3 illustrates a flow diagram of an example of a method of using the magnetic resonance system of the invention for improving the efficacy of a substance before, concomitant with, or after introduction of the substance into the subject, according to one embodiment of the invention.

FIG. 3 illustrates a flow diagram of an example of a method of using the magnetic resonance system of the invention for improving the efficacy of a substance before, concomitant with, or after administration to the subject, according to one embodiment of the invention. Method 300 may include, but is not limited to, the following steps.

Step 310: Acquiring and recording subject information and indications or conditions of interest. In this step, according to one embodiment, subject information and indications or conditions of interest acquired and recorded. For example, the operator 138 may login to the MR application 162 of the MR system server 160. In one embodiment, the operator 138 logs in using the MR web application 164. If the certain subject 150 has had previous magnetic resonance treatments, the operator 138 may retrieve subject-specific information of the certain subject 150 from the aggregate subject data 170 on the MR database 168 of the MR system server 160 via the network 140. In another example, subject data may be acquired from one or more third party networks via a third party server. Once retrieved, the subject-specific information may be stored locally in the subject data 134 of the client computer 120. If no subject-specific information is present on the MR database 168 for the certain subject 150, then the operator 138 may acquire (e.g., by oral or written questionnaire) subject-specific information. In some embodiments, the subject-specific information may include, for example, the subject's biological data, his/her indications or conditions, prescribed medication (i.e., prescribed substance 152), and/or any other information. Again, this information may be recorded in subject data 134 of the client computer 120. Method 300 may proceed to step 312.

Step 312: Acquiring substance of interest based on physician diagnosis and prescribed treatment. In this step, according to one embodiment, the operator 138 and/or subject 150 acquires a certain substance 152, which is the substance of interest for the subject's indications or conditions. For example, the operator may measure a certain dosage or reconstitute a lyophilized formulation. In various embodiments, this step can be performed at any time in the method 300. The type of substance 152 may be based on a physician's diagnosis and prescribed treatment. Method 300 may proceed to step 314.

Step 314: Querying and analyzing magnetic treatment database for positive prior treatment records and/or like-situated subjects and subject population trends. In this step, according to one embodiment, the operator 138 may submit a request for magnetic resonance treatment regimens for the subject being treated. The request may be made via the client computer 120 and transmitted to the MR system server 160. The MR system server 160 may process the request. Subsequently, the MR database 168 may be queried and analyzed for positive prior treatment records for that subject and/or like-situated subjects and subject population trends, e.g., substantially matching user information and indications. In one example, the user-specific information specifies a 42-year old, 150-pound, 5' 6" tall, Asian male taking Levodopa that is seeking treatment for Parkinson's disease. Therefore, in one embodiment, the MR analysis algorithm 166 of the MR system server 160 searches the MR reference tables 176 for one or more treatment records that are related to Parkinson's disease and to users that most closely match (e.g., in body type and/or medical history) a 42-year old, 150-pound, 5' 6" tall, Asian male taking Levodopa for Parkinson's disease. One example of the result of the query that is performed by the MR analysis algorithm 166 is shown in Table 1. Method 300 may proceed to step 316.

Step 316: Generating a recommended treatment regimen based on analysis of the magnetic treatment database. In this step, according to one embodiment, by use of the MR analysis algorithm 166 and/or the MR application 162, a recommended magnetic resonance treatment regimen can be generated that is based on the results of analyzing the information in the MR database 168. Continuing the example, one or more treatment records may be found that substantially match treatment for Parkinson's disease in combination with users that are about 42-year old, 150-pound, 5' 6" tall, and Asian male taking Levodopa for Parkinson's disease. The MR application 162 and/or MR analysis algorithm 166 of the MR system server 160 may generate a recommended magnetic resonance treatment regimen that is most suited for the certain subject 150. Further, the MR system server 160 may transmit the regimen to the client computer 120 of the requesting party. In the example of Table 1, "Record 7508" may be selected as the record that most closely matches this scenario and, thus, a treatment regimen that is substantially the same as shown in "Record 7508" is recommended. More details of a method of generating a recommended treatment regimen are described with reference to FIG. 4. Method 300 may proceed to step 318.

Step 318: Optionally, prior to starting resonation, administering certain substance of interest to the subject using a recommended method of interaction. In this step, according to one embodiment, based on the recommended magnetic resonance treatment regimen, which is computer-generated in step 314, the selected substance 152 from step 312 may be administered to the body of the subject 150 (i.e., administered) prior to starting the magnetic resonance treatment. Depending on the type of substance 152 and its intended use, the interaction between the substance 152 and subject 150 may be by ingestion, injection, and/or application of substance 152 to the surface of the skin. Method 300 may proceed to step 320. Optional step 318 may be performed instead of, or in addition to, step 322.

Step 320: Initializing magnetic resonance device settings and applying magnetic resonance to subject according to selected treatment regimen. In this step, according to one embodiment, the settings of the MR device 110 are initialized according to the selected treatment regimen. For example, the flux density, frequency, amplitude, and waveform shape of the electromagnetic energy and the resonation time can be set according to selected treatment regimen. The MR device 110 may be activated in order to apply magnetic resonance to the subject 150 according to the selected treatment regimen. Continuing the example of the 42-year old, 150-pound, 5' 6" tall, Asian male that is taking Levodopa for Parkinson's disease, the amplitude may be set to about 0.0717 the frequency may be set to about 1.8 Hertz, the waveform shape may be set to triangle, and the resonation time may be set to about 70 minutes. Or, other settings known to be effective (i.e., beneficial) may be used. In one embodiment, the MR device 110 is activated according to these settings and magnetic resonance is applied. In some cases, substance 152 is introduced during this step. Method 300 may proceed to step 322.

Step 322: Optionally, after starting resonation, introducing certain substance of interest to the subject using a recommended method of interaction. In this step, according to one embodiment, based on the recommended magnetic resonance treatment regimen, which is computer-generated in step 314, a certain substance 152 may be administered to the body of the certain subject 150 after starting the magnetic resonance treatment. Optional step 322 may be performed instead of, or in addition to, step 318. Depending on the type of substance 152 and its intended use, the interaction between the substance 152 and subject 150 may be by ingestion, injection, and/or application of substance 152 to the surface of the skin. Method 300 may proceed to step 324.

Step 324: Monitoring subject and recording efficacy of selected treatment regimen in magnetic treatment database. In this step, according to one embodiment, the subject is monitored by, for example, the operator 138. Further, the efficacy of the selected treatment regimen may be recorded. For example, the operator 138 records the efficacy in the treatment data 137 of the client computer 120. Continuing the example of the 42-year old, 150-pound, 5' 6" tall, Asian male that is taking Levodopa for Parkinson's disease, the subject is monitored by the operator 138 and the efficacy of his selected treatment regimen is recorded. In one example, the time of the onset of dyskinesias may be recorded as observed by the subject and/or the operator. Method 300 may proceed to step 326.

Step 326: Satisfactory results? In this decision step, according to one embodiment, the operator 138 examines the results of the recommended magnetic resonance treatment regimen and determines whether the results are satisfactory. Examples of factors that may influence the operator's determination include reduced or eliminated symptoms, improved performance, changes in various biofeedback data, a change in metabolites and/or biomolecules in blood or other body tissues, and/or other relevant factors. In this example, the general practitioner determines whether the 42-year old, 150-pound, 5' 6" tall, Asian male that is taking Levodopa for Parkinson's disease is having satisfactory results. If the results are satisfactory, method 300 may proceed to step 328. If the results are not satisfactory, method 300 may proceed to step 332.

Step 328: Continue treatment regimen? In this decision step, according to one embodiment, it is determined whether the specifications of the recommended magnetic resonance treatment regimen have been satisfied in order to determine whether the treatment regimen is continued. For example, it may be determined whether all of the recommended number of treatments has occurred. If treatment is to be continued, method 300 may return to step 324. If treatment is not to be continued, method 300 may proceed to step 330.

Step 330: Storing treatment data and transmitting to MR system server. In this step, according to one embodiment, the treatment data that is associated with this magnetic resonance event is stored in the treatment data 137 of the local client computer 120. Additionally, this treatment data may be transmitted to the MR system server 160 via the network 140. Further, this treatment data may be integrated into the aggregate treatment data 174 on the MR database 168. The treatment data may also be transmitted and stored on third party networks. Method 300 may end.

Step 332: Adjusting magnetic resonance device settings and continue resonating subject. In this step, according to one embodiment, the magnetic resonance treatment regimen is adjusted in order to improve the efficacy of the magnetic resonance treatment. For example, other prioritized protocols may be utilized if the recommended protocol is not satisfactory. The operator 138 and/or MR application 162 may select one of the prioritized protocols and adjustment the magnetic resonance treatment regimen accordingly. Method 300 may return to step 324.

Figure 4:
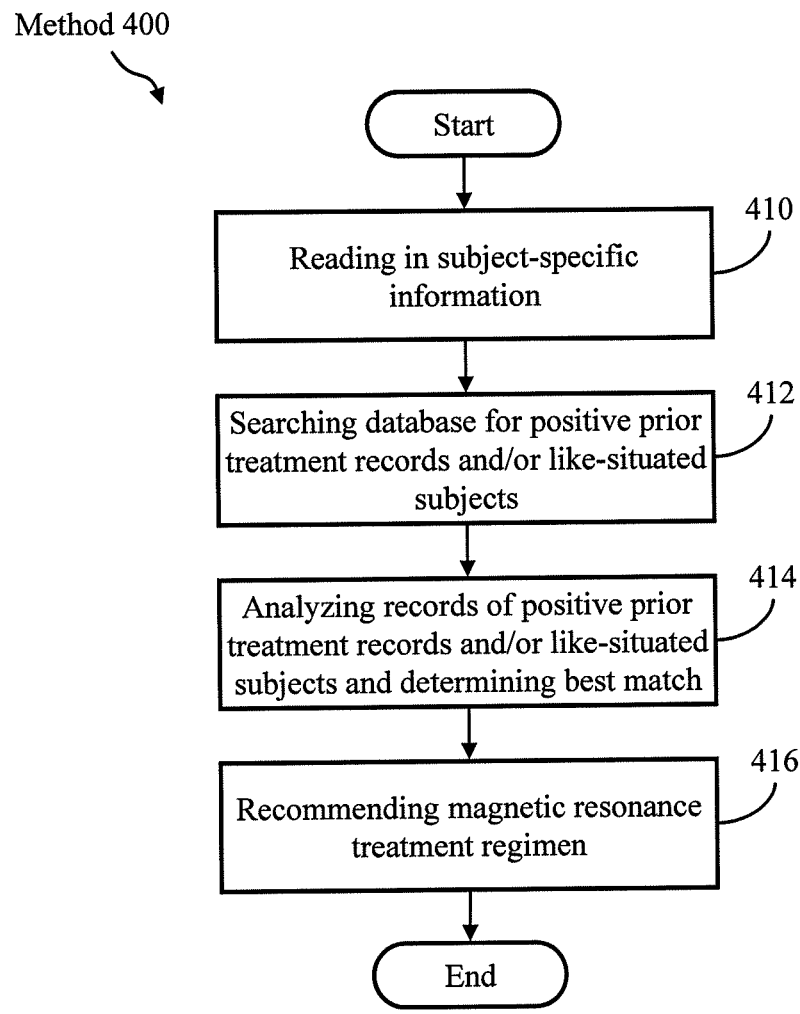
FIG. 4 illustrates a flow diagram of an example of a method of generating a recommended treatment regimen by use of the magnetic resonance system, according to one embodiment of the invention.

In an embodiment, the present invention comprises a method of generating a treatment regimen when providing MR to a subject before, concomitant with, or after administration of a substance. In one embodiment, the method comprises reading information that is specific to the subject (e.g., physical data, medical history) and encoding it into a data table of the system. The method may also comprise searching a database of the system for positive prior treatment records and/or like-situated subjects. The method may further comprise analyzing records of positive prior treatment records and/or like-situated subjects and determining the best match. The method may also comprise recommending a magnetic treatment regimen. FIG. 4 illustrates a flow diagram of an example of a method of generating a recommended treatment regimen by use of the MR system, according to one embodiment of the invention. Method 400 may include, but is not limited to the following steps.

Step 410: Reading in subject-specific information. In this step, according to one embodiment, the MR analysis algorithm 166 and/or MR application 162 of the MR system server 160 reads in the information of the subject 150 of interest. The subject-specific information may include the subject's current subject-specific data and/or prior subject-specific data, including prior magnetic resonance treatment protocols, prior physiological and subjective data, lab test results, prior medical history of illnesses, and medications previously administered. The MR analysis algorithm 166 and/or MR application 162 may search the aggregate subject data 170 of the MR database 168 and/or the subject data 134 of any client computer 120 for the most current subject-specific data available for the subject being treated. Method 400 may proceed to step 412.

Step 412: Searching database for positive prior treatment records and/or like-situated subjects. In this step, according to one embodiment, the MR analysis algorithm 166 of the MR system server 160 searches the MR database 168 for like-situated subjects. Additionally, the MR analysis algorithm 166 may use subject-specific data from like-situated subjects and subject population trends for that particular indication or condition that is stored in the MR database 168. The MR analysis algorithm 166 may use historical subject-specific data from subjects who have similar subject characteristics as the new subject, including prior physiological and subjective data, lab test results, prior medical history of illnesses, and medications previously administered. In one example, if the subject of interest is a Parkinson's subject that is using the drug Levodopa, then the MR analysis algorithm 166 may search the records of MR reference tables 176 for the terms "Indication=Parkinson's" in combination with "Substance=Levodopa," along with any combination of other subject-specific data. Method 400 may proceed to step 414.

Step 414: Analyzing records of positive prior treatment records and/or like-situated subjects and determining best match. In this step, according to one embodiment, once a subset of records that substantially match the search criteria of the like-situated subjects is assembled, the MR analysis algorithm 166 analyzes the records of like-situated subjects in order to determine substantially the best match. In one embodiment, and referring to Table 1, the MR analysis algorithm 166 may analyze the MR reference tables 176 of the MR database 168 and determine that "Record 1265" is substantially the best match as follows.

In one embodiment, in order to assemble records of interest, the MR analysis algorithm 166 executes a query against the MR database 168 in order to identify the records that substantially or partially match the subject data 134 of the subject 150. More specifically, the MR analysis algorithm 166 may query the MR database 168 and categorize records, for example, as a BEST match, GOOD match, POOR match, and NO match against the subject data 134 of interest. Furthermore, the categorization may vary from indication to indication, i.e., the criteria for categorizing the records may be indication-specific. In one example, the categorization for a Parkinson's disease (PD) patient that is taking Levodopa may be as shown in Table 2 below.

TABLE 2

Example categorization performed by MR analysis algorithm 166

| Criteria | BEST match | GOOD match | POOR match | NO match |
|---|---|---|---|---|
| Indication | PD | PD | PD | Not PD |
| Substance | Levodopa | Levodopa | Levodopa | Not Levodopa |

TABLE 2-continued

Example categorization performed by MR analysis algorithm 166

| Criteria | BEST match | GOOD match | POOR match | NO match |
|---|---|---|---|---|
| Substance dosage | 90-100% match | 75-89% match | 1-74% match | N/A |
| Age | ±5 years | ±10 years | N/A | N/A |
| Gender | Gender match | Gender match | N/A | N/A |
| Race | Race match | N/A | N/A | N/A |
| Weight | ±10 lbs | ±20 lbs | ±30 lbs | N/A |
| Height | ±2 inches | ±6 inches | ±10 inches | N/A |
| Other | Non-smoker | N/A | N/A | N/A |

Alternatively, the analysis of the MR analysis algorithm 166 may calculate a "percentage match" of the information in each record of the MR database 168 as compared with the subject data 134 of the subject 150 of interest, thereby categorizing the records. For example, in one embodiment BEST match=90-100 percentage match, GOOD match=70-89 percentage match, POOR match=40-69 percentage match, NO match=0-39 percentage match. Additionally, in calculating the percentage match, certain criterion may be weighted by importance.

Further to the example, a 59-year old, 110-pound, 5'1" tall, Asian female is seeking treatment for Parkinson's disease. The operator 138 of the client computer 120 acquires and stores the subject's subject data 134. Then, a request for MR treatment protocols for treating Parkinson's disease is sent by the operator 138 to the MR system server 160 via the network 140. The MR system server 160 processes the request that is received from client computer 120. In order to identify records of interest, the MR analysis algorithm 166 executes a query against records in the MR database 168, such as searching the subject ID for the subject of interest in order to identify prior treatment protocols that the subject has received in the past (identifying a true record match). Additionally, the MR analysis algorithm 166 searches the records for subjects that have biographical data and medical histories that are similar to the subject of interest, as those shown in Table 1, in order to determine the BEST, GOOD, POOR, and NO match records.

The result of the query and analysis of the MR analysis algorithm 166 may be a subset of records that may have a varying degree of matching relative to the subject data 134 that was the basis for the analysis. Table 1 is an example of such a subset of records for this example. The treatment protocol of the best match that is recorded to have had an overall positive feedback is then presented to the operator 138 of the client computer 120 as a recommended MR treatment protocol. A demonstration of this example is shown in "Record #1265" in Table 1, where the subject indication group, gender, race, age, weight, recreational habits, administered substance, and substance dosage is the BEST match of the subject data of the subject. Additionally, "Record #1265" contains improved feedback to the MR treatment for treatment protocol #101. Therefore, treatment protocol #101 may be presented to the operator 138 of the client computer 120 as a recommended MR treatment protocol.

In the event that the MR analysis algorithm 166 is not able to identify one or more BEST match records, the MR system server 160 may present to the operator 138 of the client computer 120 one or more GOOD match and/or POOR match records. Alternatively, the MR system server 160 may run subqueries against the MR database 168 in order to identify records which match to a certain degree the subject data 134 of the subject 150 being treated. The subqueries may run by searching limited portions of matching data (e.g., 90%, 80%, 70% of the aggregate subject and treatment data) against the MR database 168 in order to seek close match historical records with positive feedback. For example, the first subquery may eliminate "race" data as part of its search and run by searching for records that only match 90% of the data such as the indication, gender, age, weight, recreational habits, administered substance, and substance dosage of the subject for treatment protocols that have received overall positive feedback. If records containing treatment protocols that have received overall positive feedback are found to have a certain degree of matching, an additional subquery is run to rank and qualify those treatment protocols in these records by the number of sessions each treatment protocol was used. The treatment protocol used in the highest number of treatment sessions with overall positive feedback may be qualified as a GOOD match, and the treatment protocol used in the least number of treatment sessions may be qualified as a POOR match.

For example, if after running a query for historical records with positive feedback or results, the MR database 168 is unable to identify any BEST matching records, a subquery may be run using 90% of matching data against the MR database 168. This search may result in 40 close matched records containing treatment protocols that have received overall positive feedback or results. A subquery may then be run to rank and qualify the treatment protocols in each of those 40 records to identify the treatment protocol used in the highest number of sessions and the treatment protocol used in the lowest number of sessions. The MR database 168 may identify treatment protocol #104 as a GOOD match where was it used in 42 treatment sessions (the treatment protocol used in the highest number of sessions) and identify treatment protocol #108 as a POOR match where was used in only 12 treatment sessions.

Additionally, in the case that there are no close matched historical records with positive feedback when using 90% of the aggregate subject and treatment data, then a subquery may be run to look for records with 80% of the aggregate subject and treatment data. Thus, "recreational habits" data may be eliminated as part of the search. If the MR database 140 fails to find close matched historical records with positive feedback with this portion of data, then 70% of the aggregate subject and treatment data may be used, eliminating "weight" data. In the case that there are no close matched historical records with positive feedback when using 70% of the aggregate subject and treatment data, then 60% of the aggregate subject and treatment data may be used and a limit is placed on the age using an age range to search the records that are ±5 years from the age of subject being treated. If no close matched historical records with positive feedback can be located, the subqueries may continue to eliminate other portions of the data such as height, % improved feedback, subject indication group, drug dosage, and then administered drug. If no close matched historical records with positive feedback can be found, then a new record may be created.

The set of queries and subqueries described above are but one example of many different methods that could be used to find a "BEST match" and the intent is to provide a thorough example, without limiting the disclosure to this specific implementation. Method 400 may proceed to step 416.

Step 416: Recommending magnetic resonance treatment regimen. In this step, according to one embodiment, the MR analysis algorithm 166 transmits the recommended magnetic resonance treatment regimen to the requesting party. Continuing the example of the 59-year old, 110-pound, 5'1" Asian female, the MR analysis algorithm 166 may recommend substantially the same treatment regimen that is logged in "Record 1265" of Table 1. This recommendation may be transmitted via the network 140 to the client computer 120 of the requesting operator 138 or subject 150. Method 400 may end.

Thus, the present invention provides systems and methods for magnetically resonating a subject before, concomitant with, or after a substance is administered to the subject. In one aspect of the invention, magnetically resonating a subject before, concomitant with, or after a substance has been administered to the subject may provide faster and improved absorption of the substance into the subject's system. In one example, there may be faster and improved intestinal absorption.

In another aspect of the invention, magnetically resonating a subject before, concomitant with, or after a substance has been administered to the body of the subject may provide faster and improved utilization of the substance in metabolic processes and/or improved uptake by cells. In yet another aspect of the invention, magnetically resonating a subject before, concomitant with, or after a substance has been administered to the subject may provide increased absorption and/or transmission to particular target structures through electroporation. In one example, there may be enhanced penetration of chemotherapeutic agents into dense tumors.

In yet another aspect of the invention, magnetically resonating a subject before, concomitant with, or after a substance has been administered to the subject may provide improved efficacy of pharmaceuticals and/or nutraceuticals through, for example, faster absorption, improved utilization, enhanced efficacy which may be due to regulation of coherent charged states, molecular oscillation frequencies, and increased cooperativity of associated molecules.

In yet another aspect of the invention, magnetically resonating a subject before, concomitant with, or after a substance has been administered to the subject may provide enhancement of coherent waves between ordered water and macromolecular ensembles, such as proteins.

There are benefits to enhancing coherent waves between ordered water and proteins. In some embodiments, one or more benefits result from the concept that a polarized multi layer of water which is ordered can be considered to be in a semi-crystalline state. Ordered water in an organismic state has different properties than normal aqueous solutions. These properties vary in mechanical, chemical, and physical behaviors. There may be little or no interaction between bulk-phase water (non-ordered) and cellular macromolecules. Coherent charged states may therefore improve inter-atomic and inter-molecular communications which are necessary for normal cellular and intercellular communications which ultimately are based upon photon-phonon transduction, i.e., conversions of mechanical vibrations to electromagnetic oscillations and vice versa. Piezoelectricity is a general aphasic mechanism responsible for maintaining the necessary communications systems (cooperatively) between molecules and cells, most especially signaling across cell membranes by critical molecules such as hormones, antibodies and neurotransmitters, which may then be continued by second messenger systems, e.g., reception tyrosine kinases, receptor serine/threonine kinases, receptor guanylyl cyclases, or histidine-kinase-associated receptors.

Thus, ordered water through polarized waves such as solutions for example, may enhance second messenger systems, including, for example, G proteins, phospholipase C, Grb2, adenylate cyclase, IP3, diacylglycerol (critical to lipid and carbohydrate metabolism), or MAP-kinase, which serve to communicate messages of critical molecules forming the receptor-ligand association at the membrane surface, to gene regulatory proteins and many target proteins—thus facilitating normal electrophysiological function thus enhancing health and well being. Thus, electromagnetic resonation of water may imbue a coherent charged state which enhances the signal transductive mechanisms of biologically ordered matter to therein improve interactivity of macromolecular assemblages.

In yet another aspect of the invention, magnetically resonating a subject before, concomitant with, or after a substance has been administered to the body of the subject may provide improved solvency of water in living systems. Treating the entire living system before and/or during the introduction of a substance into the subject may improve the utilization of the substance.

In yet another aspect of the invention, with improved penetration and utilization of pharmaceuticals and/or nutraceuticals that may be provided by the system and methods of the invention, there may be improved efficacy of drug therapies, which may lead to lower dosages, fewer side effects, and reduced cost of the drug therapies.

EXAMPLES

Example 1

Parkinson's

It has been demonstrated that resonating a Parkinson's patient after he/she has consumed, for example, the Parkinson's drug Levodopa, commonly referred to as Sinemet, has improved the absorption rate of Levodopa and, thus, has improved the efficacy of Levodopa.

In this example, involuntary movements, called dyskinesias, is an observable side effect of introducing Levodopa into the body of the patient. A Parkinson's patient may consume a certain dosage of Levodopa along with no magnetic resonance and is observed to experience dyskinesias after about 38 minutes from consuming Levodopa. By contrast, the same Parkinson's patient may consume substantially the same dosage of Levodopa and then receives magnetic resonance and is observed to experience dyskinesias after about 22 minutes from consuming Levodopa. Additionally, the magnetic resonance may enable the patient to significantly reduce the amount of the drug needed to produce the desired result. This shows that using magnetic resonance after Levodopa is administered to the patient improves the absorption rate of Levodopa into the body systems of the patient.

For this protocol, the MR device settings may be, for example, within a window or discrete opportunity of amplitude, such that the B field is about 0.065 microgauss to about 0.078 microgauss, and within a discrete range of about 1.8 Hz to 7.8 Hz, with the waveform parameter set to sinusoidal, and the MR treatment duration parameter set to about 60 minutes.

Example 2

Cardiac Arrythmias

It may be demonstrated that resonating cardiac arrhythmias subjects after consuming one of the Beta blocker drugs (or Beta-adrenergic blocking agents) has the effect of, for example, enhancing the action of the drug, provides faster absorption, provides faster utilization, provides greater efficacy in refractory cases, and reduces dosage requirements, which reduces side effects.

Cardiac arrhythmia is, for example, atrial fibrillation, tachycardia, and ectopic beat. Beta blockers belong to the drug class: antiadrenergic, antianginal, antiarrhythmic, and antihypertensive. Examples of Beta blockers include, but are not limited to, amiodarone, Beta-adrenergic blocking agents, calcium channel blockers, disopyramide, dofetilide, flecamide acetate, mexiletine, moricizine, procainamide, propefenone, quinidine, and tocamide, which may be available in tablet form, liquid form, and extended-release caplet/tablet form.

The actions of these drugs include blocking sympathetic nervous system, lowering the heart's oxygen requirement, slowing nerve impulses through the heart, and reducing blood vessel contraction in the heart.

Observable benefits of resonating cardiac arrhythmias patients after consuming one of the Beta blocker drugs may include the reduction of dosage requirements, which consequently reduces side effects, such as nausea, weakness, diarrhea, shortness of breath, rapid heartbeat, risk of asthma, pulse rate slower than 50 beats/minute, cold hands/feet, dry mouth, dry eyes, dry skin, hallucinations, nightmares, insomnia, confusion, and constipation.

Another observable benefit of resonating cardiac arrhythmias patients after consuming one of the Beta blocker drugs may include the reduction or elimination of the risk of, for example, rash, sore throat and fever, unusual bleeding and bruising, dry burning eyes, hallucinations, nightmares, insomnia, and rapid heartbeat.

For this protocol, the MR device settings may be, for example, amplitude=about 0.031 µG to about 0.0325 µG, frequency=about 0.857 Hz to about 0.91 Hz, waveform=sinusoidal, and MR treatment duration=about 30 minutes.

Example 3

Cancer

It may be demonstrated that resonating cancer patients after consuming one of the cancer drugs has the effect of, for example, enhancing the action of the drug, provides faster absorption, provides faster utilization, provides greater efficacy in refractory cases, and reduces dosage requirements, which reduces side effects.

Cancer drugs include, for example, tamoxifen, aminoglutethimide, antiandrogens (non-steroidal), busulfan, capecitabine, chlorambucil, cyclophosphamide, estramustine, etoposide, hydroxyurea, imatinib, lomustine, mephalan, mercaptopurine, mitotane, paclitaxel, procarbozine.

In one example, carboplaton and taxol are cancer drugs for treating cancer, including ovarian cancer. In one example, a Caucasian female over fifty years old reported increased lethargy and decreased energy and motivation after taking the cancer drugs.

The subject was treated for 1.5 hours daily when possible for approximately one year. Observable benefits of resonating the subject before, after, and/or concomitant with consuming one or both of the above-referenced drugs included an improvement in energy levels, sleep, mental alertness, and a significant reduction in pain. The subject was also able to extend the period in which she received chemotherapy and is currently in complete remission. In various embodiments, the benefits of resonating the subject may include improved targeting of dense tumors through electroporation of tumors, increasing the absorption rate, enhancing utilization through electroporation of tissues, drug targeting is more readily accomplished, reducing risk of impairing immune system function, and improving the subject's quality of life.

Another observable benefit of resonating cancer (neuplasia) patients after consuming one of the cancer drugs may include the reduction of dosage requirements, which consequently reduces side effects, such as leg pain, shortness of breath, hot flashes, nausea, vomiting, weight gain, dry skin, menstrual irregularities, vaginal itching, sleepiness, blurred vision, and confusion.

For this protocol, the MR device settings may be, for example, amplitude=about 0.017 µG to about 0.3 µG, frequency=about 0.3 Hz to about 9.6 Hz, waveform=sine or square, and MR treatment duration=about 80 minutes.

Example 4

Diabetes

It may be demonstrated that resonating diabetes patients after consuming a diabetes drug has the effect of, for example, enhancing the action of the drug, provides faster absorption, provides faster utilization, and reduces dosage requirements, which reduces side effects.

In one example, sulfonylureas is a class of diabetes drug that may be used for treating diabetes in adults who are unable to control blood sugar by diet, weight loss and exercise and for treating diabetes insipidus. Sulfonylureas may be available in tablet form and extended-release tablet form. Other classes of diabetes drugs include meglitinides, biguanides, thiazolidinediones, and alpha-glucosidase inhibitors.

In certain embodiments, MR treatment of the subject prior to, during or after consuming a diabetes drug results in a reduction in blood sugar as compared to subjects who consume the same drug and are not exposed to MR. Other observable benefits of resonating diabetes patients after consuming, for example, sulfonylureas may include the reduction of dosage requirements, which consequently reduces side effects, such as hunger, anxiety, cold sweats, rapid pulse, shortness of breath, headache, fatigue, itchy skin, rash, sore throat and fever, ringing in ears, unusual bleeding and bruising, and edema confusion.

For this protocol, the MR device settings may be, for example, amplitude=about 0.075 µG to about 0.4998 µG, and frequency=about 2.1 Hz to about 7.8 Hz, waveform=sine, and MR treatment duration=about 1 to 1.5 hour were used.

Example 5

Diabetes

In this study, the MR device settings ranging from an amplitude=about 0.49980 to 0.075 µG, frequency=about 2.1 Hz to about 13.9996 Hz, waveform=sine, and MR treatment duration=about 1 to 1.5 hours were used to treat six subjects who were receiving oral medication for diabetes. The components evaluated were A1c (Glycated Hemoglobin or HbA1c), FBS (fasting blood sugar), and triglycerides. These components were measured by an independent, commercial testing laboratory. The components were measured at time 0 (i.e., just prior to beginning MR treatment) and 13 weeks after MR treatment was begun. Treatments were for about 1 to 1.5 hours three times per week. As shown by the data presented below, it was found that patients undergoing MR treatment exhibited both statistically significant (using the T-test for two correlated samples) and clinically significant improvement in the levels of A1c.

TABLE 3

MEAN & STANDARD DEVIATIONS FOR A1c

| n = 6 | A1c | | FBS | | Triglycerides | |
|---|---|---|---|---|---|---|
| | Baseline | 13 weeks | Baseline | 13 weeks | Baseline | 13 weeks |
| Mean | 9.87 | 8.57 | 196.67 | 160.17 | 251.50 | 147.83 |
| Std. Dev. | 1.83 | 1.45 | 68.56 | 35.10 | 177.60 | 84.75 |

T-TEST FOR 2 CORRELATED SAMPLES FOR A1c, FBS & TRIGLYCERIDES

| Target | Results |
|---|---|
| A1c | $\mu a - \mu b = 1.3$ (the difference between the 2 means); $t = +4.42$; $df = 5$ $p$(one-tailed) = 0.0034 => $p < 0.005$ => statistically significant $p$(two-tailed) = 0.0069 => $p < 0.01$ => statistically significant |

Example 6

Diabetic Neuropathy

It has been demonstrated that resonating diabetic peripheral neuropathy patients before, after, and/or concomitant with consuming diabetic neuropathy drugs has beneficial effects.

In one subject, a 62-year-old Caucasian male suffered with diabetic neuropathy in both feet. The subject had a total lack of sensation with burning and pain for three to four years. The subject was taking the drugs Actos, Metaformin, and Lisinopril. The subject was resonated four times for one hour each time. The result of this treatment was that sensation returned for touch, texture, and temperature. As of fifteen months after the last treatment session, the sensation remained. Also, the subjects from Example 5 reported improvements with respect to symptoms relating to diabetic neuropathy (e.g., lack of sensation and pain).

In providing MR treatment to a subject with diabetic neuropathy, an amplitude of about 0.455 μG to about 0.53 μG, with a frequency of about 12.7 Hz to about 14.84 Hz may be used.

Example 7

Arthritis

It may be demonstrated that resonating osteoarthritis patients before, concomitant with, and/or after consuming one of the osteoarthritis drugs has the effect of, for example, enhancing the action of the drug, provides faster absorption, provides faster utilization, and reduces dosage requirements, which reduces side effects.

In one example, a 72-year-old Caucasian female suffered from back pain due to degenerative disk disease in her low back and sciatica. The subject was taking the following drugs: Aspirin, Ibuprofin, and Naproxen. The subject was resonated approximately three times per week for more than one year. The results of this continuing treatment include significantly less pain, an improved range of motion, and improved sleep.

In another example, a 72-year-old Caucasian male experienced arthritis pain in a number of joints, including his hips, hands, and shoulders. The subject also suffered from sciatica in his hips and legs. The subject was taking Celebrex. The subject was resonated at least three times per week for one to two hours per session. The results included a reduction in dosage and frequency of taking Celebrex, decreased pain, improved mobility, and improved sleep.

In a further example, a fifty-year-old Caucasian female experienced osteoarthritis pain and stiffness in her hands and finger joints. The subject was taking Aspirin and Ibuprofin. The subject was resonated twice for one-half hour per treatment. The subject was asked to rate her pain on a scale of zero (feels great) to ten (feels terrible) before and after treatment. Before treatment, the subject characterized the stiffness in her hand at two; after treatment she characterized it as zero. Before treatment, the subject characterized the pain in her thumb at three; after treatment she characterized it as zero.

In some embodiments, aspirin is an osteoarthritis drug for treating swelling, stiffness, joint pain of arthritis or rheumatism; pain, fever, and inflammation. Aspirin may be available in tablet form and extended-release tablet form.

Observable benefits of resonating osteoarthritis patients after consuming, for example, aspirin may include faster and more effective pain reduction and stiffness reduction, better utilization, and faster absorption.

Another observable benefit of resonating osteoarthritis patients after consuming, for example, aspirin may include the reduction of dosage requirements, which consequently reduces side effects, such as black/bloody vomit, blood in urine, difficulty breathing, hives, rash, itching due to allergic response, heartburn, indigestion, nausea and vomiting, insomnia, and rectal irritation.

For this protocol, the MR device settings may be, for example, amplitude=about 0.031 μG to about 0.457 μG, frequency=about 0.852 Hz to about 18 Hz, waveform=sinusoidal, rectilinear, square, and MR treatment duration=about 60 minutes. Alternatively, an amplitude of about 0.01 μG to about 0.46 μG, with a frequency of about 0.2799 Hz to about 12.8765 Hz may be used.

Example 8

Migraines and Headaches

It may be demonstrated that resonating migraine and headache patients before, concomitant with, and/or after consuming a drug has the effect of, for example, enhancing the action of the drug, provides faster absorption, provides faster utilization, and reduces dosage requirements, which reduces side effects.

In one example, a 48-year-old Caucasian female experienced migraines for many years, including a recent worsening due to exposure to large amounts of new carpet and glue. The subject took the following drugs: Topomax (daily), Immitrex PRN, and Ibuprofin. The subject was resonated ten times for 1 to 1.5 hours per treatment over a one-month period. The results included a decreased frequency and duration of migraines as well as a reduction in the subject's use of PRN pain medications. Before being resonated, the subject described her pain level being at nine on a scale of zero to ten (zero being no pain and ten being the highest amount of pain). After treatment, the subject described her pain level as two.

In another example, a seventeen-year-old Caucasian female experienced pain associated with migraines. The subject took the following drugs: Topomax, Immitrex, and Ibuprofin. The subject received two one-hour treatments three months apart. The result of the treatments was a reduction in pain level by 50% and a reduced dosage of drugs.

In a further example, a 48-year-old Caucasian female experienced pain associated with severe headaches. The subject took Aspirin to treat the pain. The subject received one treatment for one hour. The result was a reduction in pain from 6.5 to zero.

In providing MR treatment to a subject with migraines and/or headaches, an amplitude of about 0.015 µG to about 0.034 µG, with a frequency of about 0.3219 Hz to about 0.95174 Hz may be used.

Example 9

Fibromyalgia

It may be demonstrated that resonating fibromyalgia patients before, concomitant with, and/or after consuming a drug has the effect of, for example, enhancing the action of the drug, provides faster absorption, provides faster utilization, and reduces dosage requirements, which reduces side effects.

In one example, a 51-year-old Caucasian male experienced fibromyalgia for a number of years. The subject also experienced insomnia, restless legs, and chronic fatigue. The subject took the drug Naproxen (Aleve). The subject received seven consecutive days of 1 to 1.5 hour treatments. Before receiving the treatments, the subject characterized his initial pain levels ranging from three to seven, depending on the area of the body. After completing treatment, the subject described his pain level as zero to one. The subject described less burning sensations throughout his body, with the significant reduction lasting two to three months after his last treatment.

In another example, a 48-year-old Caucasian male suffered from fibromyalgia, pituitary failure, myopathy, chronic sinusitis, chronic fatigue, HTN, and had received low back surgery. His primary complaint was back pain. The subject was on the following drugs: Robaxin, Morphine, Dilaudid, Lyrica, Clonazepam, lidoderm, Lisinopril, HCTZ, Nifedipine, Claritin, and Flonase. The subject received thirteen treatments within a two-month period. He described his pre-treatment pain level as 4; and after treatment his pain level was 0.5. Approximately two months after completing his first series of treatment, he began a second regimen of ten treatments within a two-month period. Before beginning the second series, he described his initial pain level as 4; and after completing treatment he described it as 0 to 1. The subject also described taking significantly less pain medication after completing the second series of treatments.

In a further example, a Caucasian female at least fifty years old suffered from fibromyalgia for a number of years. The subject did not take drugs specifically for fibromyalgia, but took Naproxen (Aleve). The subject received daily (when possible) treatments for approximately one year. Before treatment, the subject described her pain level as six. After treatment, she described a total elimination of pain.

In providing MR treatment to a subject with fibromyalgia, an amplitude of about 0.3 µG to about 0.46 µG, with a frequency of about 8.3977 Hz to about 12.87 Hz may be used.

Example 10

Injuries

It may be demonstrated that resonating injured patients before, concomitant with, and/or after consuming a drug has the effect of, for example, enhancing the action of the drug, provides faster absorption, provides faster utilization, and reduces dosage requirements, which reduces side effects.

In one example, a Causian male over 55 years old experienced severe overall pain—including pain in his shoulders, back, leg, and neck—due to an automobile accident. The subject was taking one or more pain medications. The subject received 38 treatments over the course of one year. The results included an overall improvement in mobility and improved sleep. Also, before receiving treatment, the subject described an initial pain level of five, on a scale of zero to ten. After completing treatment, the subject described his pain level as 0 to 2.5.

In another example, a fifty-year-old Caucasian male experienced pain and stiffness associated with a shoulder injury. The subject was taking Aspirin and Ibuprofin. The subject received two one-hour treatments three days apart. The result was a decrease in pain level of 50% and a decrease in stiffness of 50%.

In a further example, a 45-year-old Caucasian male experienced pain and stiffness associated with an injured knee. The subject was taking Aspirin and Ibuprofin. Over the course of 5 days, the subject received 3 treatments, each lasting 1.5 hours. The result was a decrease in pain level of 50-100% and a decrease in stiffness of 50%.

In a further example, a 48-year-old Caucasian male experienced pain and stiffness associated with an injured right knee that was the result of an old Meniscus tear injury. The subject was taking Aspirin and Ibuprofin. Over the course of 5 days, the subject received 3 treatments, each lasting 1 hour. The result was a 100% elimination of his pain an stiffness.

In another example, a 49-year-old Caucasian male experienced pain and stiffness associated with an injured left knee. The subject was taking Aspirin and Ibuprofin. Over the course of three days, the subject received two treatments, each lasting one hour. The result was a decrease in pain level of 75% and a decrease in stiffness of 50%.

In providing MR treatment to a subject with pain and/or one or more injuries, an amplitude of about 0.01 µG to about 0.5 µG, with a frequency of about 0.2799 Hz to about 14.0 Hz may be used.

Example 11

Back Pain

It may be demonstrated that resonating injured patients before, concomitant with, and/or after consuming a drug has the effect of, for example, enhancing the action of the drug, provides faster absorption, provides faster utilization, and reduces dosage requirements, which reduces side effects.

In one example, a 48-year-old Caucasian female experienced pain and stiffness associated with her low back. The subject was taking Aspirin and Ibuprofen. Over the course of ten days, the subject received three treatments. The result was a decrease in pain level of 50-100%.

In another example, a 48-year-old Caucasian female experienced pain and stiffness associated with her low back. The subject was taking Aspirin and Ibuprofen. Over the course of eleven days, the subject received four treatments, each lasting one hour. The result was a decrease in pain level and stiffness level of 75%.

In another example, a 41-year-old Caucasian male experienced pain and stiffness associated with his low back. The subject was taking Aspirin and Ibuprofen. The subject received one treatment, lasting one hour. The result was a decrease in pain level of 60-70% and stiffness level of 90%.

In providing MR treatment to a subject with back pain, an amplitude of about 0.01 µG to about 0.457 µG, with a frequency of about 0.2799 Hz to about 12.8 Hz may be used.

Example 12

Cholesterol

It may be demonstrated that resonating patients with high cholesterol before, concomitant with, and/or after consuming a drug has the effect of, for example, enhancing the action of the drug, provides faster absorption, provides faster utilization, and reduces dosage requirements, which reduces side effects.

In one example, a 73-year-old Caucasian male was taking the drug Lipitor to manage his cholesterol levels. The subject began a series of three treatments per week for twenty months, and continuing on an ongoing basis. The result is that the subject's cholesterol levels are at the best ratio in twenty years.

In order to provide MR treatment for cholesterol, the MR device settings may range from an amplitude from about 0.4998 µG to about 0.075 µG and a frequency from about 2.1 Hz to about 13.9996 Hz, or ranges within these ranges.

Example 13

Prostate

It may be demonstrated that resonating patients with prostate problems, such as an enlarged prostate, before, concomitant with, and/or after consuming a drug has the effect of, for example, enhancing the action of the drug, provides faster absorption, provides faster utilization, and reduces dosage requirements, which reduces side effects.

In one example, a 73-year-old Caucasian male had been diagnosed with an enlarged prostate for fifteen years and his PSA count was rising (the last measurement was 2.35). The subject was taking the drugs Avodart and Flomax. The subject began a series of three treatments per week for twenty months, and continuing on an ongoing basis. The result is that after eighteen months of treatment, his prostate was no longer enlarged and his PSA count was down to 0.95 (his lowest level in thirteen years).

In providing MR treatment to a subject with prostate problems, an amplitude of about 0.01 µG to about 0.4 µG, with a frequency of about 0.2799 Hz to about 11.197 Hz may be used.

From the foregoing, one of ordinary skill in the art will appreciate that the present disclosure sets forth systems and methods for magnetically resonating both a subject and a substance administered to the body of the subject. The teachings of this disclosure shall not be considered to be limited to the specific examples disclosed herein, but to include all applications within the spirit and scope of the invention.

What is claimed is:

1. A method of using a magnetic resonance system comprising:
   administering a substance to a subject, wherein the substance is a drug administered as part of a treatment regimen; and
   providing a resonant magnetic field to the subject either before, concomitant with, or after administration of the substance;
   monitoring the effect of the resonant magnetic field on the subject;
   monitoring the effect of the substance on the subject; and
   monitoring the interacting components of the resonant magnetic field and the substance on the subject concomitant with one another in order to determine how the application of the resonant magnetic field effects an absorption rate of the drug by the subject.

2. The method of claim 1, further comprising the initial step of generating a treatment regimen based on analyzing data associated with the subject.

3. The method of claim 2, wherein generating a treatment regimen based on analyzing data associated with the subject comprises the steps of:
   analyzing data for positive prior treatment records of the subject; and
   determining the treatment regimen that is the best match to the subject.

4. The method of claim 2, wherein generating a treatment regimen based on analyzing data associated with the subject comprises the steps of:
   analyzing data for positive prior treatment records of like-situated subjects; and
   determining the treatment regimen that is the best match to the subject.

5. The method of claim 2, wherein generating a treatment regimen based on analyzing data associated with the subject comprises the steps of:
   analyzing subject population trends; and
   determining the treatment regimen that is the best match to the subject.

6. The method of claim 1, wherein the substance is administered after the resonant magnetic field has begun to be provided.

7. The method of claim 1, wherein the substance is administered before the resonant magnetic field has begun to be provided.

8. The method of claim 1, wherein the substance is administered concomitant with providing the resonant magnetic field.

9. The method of claim 1, wherein the subject is monitored before, during, or after the treatment.

10. The method of claim 9, further comprising making the decision to continue or end treatment based at least in part on the monitoring of the subject.

11. The method of claim 9, further comprising adjusting the treatment regimen based at least in part on the monitoring of the subject.

12. The method of claim 1, further comprising the step of storing data concerning the treatment regimen.

13. A method of treating a human, animal, or plant subject with a magnetic resonance system, the method comprising:
   administering a substance and resonant magnetic field to a subject, wherein the substance is a drug administered as part of a treatment regimen, and wherein the magnetic field is given before, after, or concomitant with the substance;
   monitoring the effect of the resonant magnetic field on the subject;
   monitoring the effect of the substance on the subject; and
   monitoring the interacting components of the resonant magnetic field and the substance on the subject concomitant with one another in order to determine how the application of the resonant magnetic field effects an absorption rate of the drug by the subject.

14. The method of claim 13, wherein the subject has an indication or symptom of a medical condition.

15. The method of claim 14, wherein the substance is a beneficial substance, such that the substance has the capacity to ameliorate at least in part a symptom associated with the medical condition.

16. The method of claim 14 wherein the indication comprises at least one of Parkinson's disease, diabetes, cancer, osteoarthritis, migraine, headache, fibromyalgia, chronic fatigue syndrome, pain, sports injury, accident injury, stiffness, back pain, diabetic neuropathy, high cholesterol, enlarged prostate, cardiac arrhythmia, tachycardia, atrial fibrillation, ventricular fibrillation, AIDS, Alzheimer's disease, multiple sclerosis, amyotrophic lateral sclerosis, muscular dystrophy, attention deficit disorder, attention deficit hyperactive disorder, cerebral palsy, depression, or schizophrenia.

17. The method of claim 13, wherein the substance comprises at least one of Levodopa, beta blockers, cancer drugs, diabetes drugs, sulfonylureas, meglitinides, biguanides, thiazolidinediones, and alpha-glucosidase inhibitors, aspirin, ibuprofen, migraine drugs, pain relievers, Naproxen, cholesterol drugs, or prostate drugs.

18. The method of claim 13, wherein administering magnetic resonance comprises providing a resonant magnetic field with a flux density range of about 1 gauss to about $10^{-50}$ gauss with the magnetic resonance system.

19. The method of claim 13, wherein administering magnetic resonance comprises providing a resonant magnetic field with a flux density range of about $10^{-5}$ gauss to about $10^{-12}$ gauss with the magnetic resonance system.

20. The method of claim 13, wherein the indication comprises Parkinson's disease.

21. The method of claim 20, wherein administering magnetic resonance comprises providing a resonant magnetic field with a flux density range of about $6.6\times10^{-8}$ gauss to about $7.8\times10^{-8}$ gauss with the magnetic resonance system.

22. The method of claim 20, wherein administering magnetic resonance comprises providing a resonant magnetic field with a frequency range of about 1.8 Hz to about 140 Hz with the magnetic resonance system.

23. The method of claim 14, wherein the indication comprises the medical condition of diabetes.

24. The method of claim 23, wherein administering magnetic therapy comprises providing a resonant magnetic field with a flux density range of about $5\times10^{-7}$ gauss to about $1\times10^{-8}$ gauss with the magnetic resonance system.

25. The method of claim 23, wherein administering magnetic resonance comprises providing a resonant magnetic field with a flux density range of about $5\times10^{-7}$ gauss to about $1\times10^{-8}$ gauss and a frequency range of from about 2.156 Hz to about 13.992 Hz with the magnetic resonance system.

26. A method of treating a subject with a magnetic resonance system that reduces the amount of a beneficial substance required to achieve a result or that increases the efficacy of an amount of the beneficial substance, the method comprising:
 exposing the subject to a resonant magnetic field before, concomitant with, or after the administration of the beneficial substance, wherein the substance is a drug administered as part of a treatment regimen;
 monitoring the effect of the resonant magnetic field on the subject;
 monitoring the effect of the substance on the subject; and
 monitoring the interacting components of the resonant magnetic field and the substance on the subject concomitant with one another in order to determine how the application of the resonant magnetic field effects an absorption rate of the drug by the subject.

* * * * *